(12) United States Patent
Campbell et al.

(10) Patent No.: US 10,016,579 B2
(45) Date of Patent: Jul. 10, 2018

(54) CONTROLLABLE INFLATION PROFILE BALLOON COVER APPARATUS

(75) Inventors: Carey V. Campbell, Flagstaff, AZ (US); James L. Goepfrich, Flagstaff, AZ (US); Brandon C. Hedberg, Flagstaff, AZ (US); Benjamin M. Trapp, Flagstaff, AZ (US)

(73) Assignee: W.L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 13/619,806

(22) Filed: Sep. 14, 2012

(65) Prior Publication Data

US 2013/0253466 A1    Sep. 26, 2013

Related U.S. Application Data

(63) Continuation-in-part of application No. 13/529,896, filed on Jun. 21, 2012.
(Continued)

(51) Int. Cl.
*A61M 25/10* (2013.01)
*A61F 2/958* (2013.01)

(52) U.S. Cl.
CPC ............ *A61M 25/10* (2013.01); *A61F 2/958* (2013.01); *A61M 25/1029* (2013.01); *A61M 25/104* (2013.01); *A61M 2025/1031* (2013.01); *A61M 2025/1075* (2013.01); *A61M 2025/1081* (2013.01); *F04C 2270/041* (2013.01)

(58) Field of Classification Search
CPC ................ A61M 25/10; A61M 25/104; A61M 25/1029; A61M 2025/1031; A61M 2025/1075; A61M 2025/1081; A61M 2025/1068

USPC .... 604/101.01, 101.02, 103.11–103.14, 103, 604/103.01, 103.02, 103.04–103.09; 606/192, 194
See application file for complete search history.

(56) References Cited

U.S. PATENT DOCUMENTS 4,738,666 A   4/1988   Fuqua
5,104,376 A   4/1992   Crittenden
(Continued)

FOREIGN PATENT DOCUMENTS

EP    0457456 A1   11/1991
JP    8033720      2/1996
(Continued)

OTHER PUBLICATIONS

International Search Report and Written Opinion for PCT/US2012/055666 dated May 2, 2013, corresponding to U.S. Appl. No. 13/619,806.
(Continued)

*Primary Examiner* — Andrew Gilbert
(74) *Attorney, Agent, or Firm* — Kilpatrick Townsend & Stockton. LLP

(57) ABSTRACT

Embodiments are presented of a balloon assembly operable to provide a balloon diameter vs. balloon pressure profile generally depicting a balloon inflation sequence providing at least one intermediate inflated diameter and a final inflated diameter of a balloon such that the balloon attains the at least one intermediate diameter at a predetermined pressure, and attains the final diameter at a final predetermined pressure that is lower than a predetermined pressure of a last intermediate pressure.

52 Claims, 29 Drawing Sheets

Related U.S. Application Data

(60) Provisional application No. 61/500,555, filed on Jun. 23, 2011, provisional application No. 61/535,864, filed on Sep. 16, 2011.

(56) References Cited

U.S. PATENT DOCUMENTS

| | | | |
|---|---|---|---|
| 5,116,318 A | 5/1992 | Hillstead | |
| 5,137,512 A | 8/1992 | Burns et al. | |
| 5,324,261 A | 6/1994 | Amundson et al. | |
| 5,348,538 A | 9/1994 | Wang et al. | |
| 5,358,486 A | 10/1994 | Saab | |
| 5,358,487 A * | 10/1994 | Miller | A61M 25/1011 604/101.02 |
| 5,443,495 A | 8/1995 | Buscemi et al. | |
| 5,447,497 A * | 9/1995 | Sogard | A61M 25/1011 604/101.02 |
| 5,458,615 A | 10/1995 | Klemm et al. | |
| 5,507,768 A | 4/1996 | Lau et al. | |
| 5,545,209 A | 8/1996 | Roberts et al. | |
| 5,647,857 A * | 7/1997 | Anderson | A61F 2/958 604/160 |
| 5,752,934 A * | 5/1998 | Campbell | A61L 29/085 604/96.01 |
| 5,755,769 A * | 5/1998 | Richard | A61F 2/90 623/1.2 |
| 5,843,027 A | 12/1998 | Stone et al. | |
| 5,868,704 A | 2/1999 | Campbell et al. | |
| 5,873,880 A | 2/1999 | Williams et al. | |
| 5,879,369 A * | 3/1999 | Ishida | A61M 25/10 604/96.01 |
| 5,964,730 A | 10/1999 | Williams et al. | |
| 5,980,531 A * | 11/1999 | Goodin | A61F 2/958 604/101.01 |
| 6,096,056 A * | 8/2000 | Brown | A61F 2/958 606/108 |
| 6,123,712 A * | 9/2000 | Di Caprio | A61F 2/95 606/108 |
| 6,432,130 B1 * | 8/2002 | Hanson | A61F 2/958 606/194 |
| 6,537,247 B2 | 3/2003 | Shannon | |
| 6,613,067 B1 * | 9/2003 | Johnson | A61F 2/0095 604/103.11 |
| 6,656,213 B2 | 12/2003 | Solem | |
| 6,695,863 B1 | 2/2004 | Ramzipoor et al. | |
| 6,746,425 B1 | 6/2004 | Beckham | |
| 6,749,584 B2 | 6/2004 | Briggs et al. | |
| 6,756,094 B1 | 6/2004 | Wang et al. | |
| 6,756,096 B2 * | 6/2004 | Harding | B31D 5/0047 428/192 |
| 6,790,224 B2 * | 9/2004 | Gerberding | A61F 2/958 623/1.12 |
| 6,899,727 B2 * | 5/2005 | Armstrong | A61F 2/95 623/1.12 |
| 6,923,827 B2 | 8/2005 | Campbell et al. | |
| 6,955,658 B2 | 10/2005 | Murray, III | |
| 7,108,684 B2 | 9/2006 | Farnan | |
| 7,195,638 B1 | 3/2007 | Sridharan | |
| 7,641,844 B2 | 1/2010 | Melsheimer | |
| 7,727,191 B2 * | 6/2010 | Mihalik | A61B 18/02 604/101.01 |
| 7,942,847 B2 * | 5/2011 | Stupecky | A61M 25/10 604/103.06 |
| 8,016,752 B2 * | 9/2011 | Armstrong | A61M 25/0043 600/156 |
| 8,388,599 B2 * | 3/2013 | Warnack | A61M 25/10 604/101.02 |
| 8,460,240 B2 | 6/2013 | Towler | |
| 2002/0052640 A1 * | 5/2002 | Bigus | A61F 2/07 623/1.11 |
| 2002/0098307 A1 * | 7/2002 | Schwartz | A61L 29/14 428/36.3 |
| 2003/0093086 A1 | 5/2003 | Briggs et al. | |
| 2003/0211258 A1 | 11/2003 | Sridharan et al. | |
| 2004/0170782 A1 * | 9/2004 | Wang | A61L 29/041 428/35.2 |
| 2005/0124969 A1 | 6/2005 | Fitzgerald et al. | |
| 2007/0073328 A1 * | 3/2007 | Kennedy, II | A61M 25/10 606/192 |
| 2007/0083216 A1 | 4/2007 | Belef et al. | |
| 2007/0135829 A1 * | 6/2007 | Paganon | A61F 5/003 606/192 |
| 2007/0213759 A1 | 9/2007 | Osborne et al. | |
| 2007/0232996 A1 | 10/2007 | Andersen | |
| 2008/0033476 A1 * | 2/2008 | Greene | A61M 25/1011 606/194 |
| 2008/0033477 A1 | 2/2008 | Campbell et al. | |
| 2008/0097301 A1 | 4/2008 | Alpini et al. | |
| 2008/0103444 A1 | 5/2008 | Jimenez | |
| 2008/0140173 A1 | 6/2008 | Eskaros et al. | |
| 2008/0319388 A1 | 12/2008 | Slattery et al. | |
| 2009/0043254 A1 | 2/2009 | Pepper et al. | |
| 2009/0076449 A1 | 3/2009 | Geis et al. | |
| 2009/0088725 A1 * | 4/2009 | Bataille | A61M 25/0662 604/509 |
| 2009/0112159 A1 | 4/2009 | Slattery et al. | |
| 2009/0227948 A1 * | 9/2009 | Chen | A61L 29/085 604/103.02 |
| 2009/0299327 A1 * | 12/2009 | Tilson | A61B 17/8816 604/500 |
| 2010/0010303 A1 | 1/2010 | Bakos | |
| 2010/0057001 A1 | 3/2010 | Chen et al. | |
| 2010/0228333 A1 | 9/2010 | Drasler et al. | |
| 2010/0318029 A1 | 12/2010 | Pepper et al. | |
| 2011/0144583 A1 * | 6/2011 | Matov et al. | 604/103.05 |
| 2013/0253466 A1 * | 9/2013 | Campbell | A61M 25/10 604/500 |

FOREIGN PATENT DOCUMENTS

| | | |
|---|---|---|
| JP | 2005-230535 | 9/2005 |
| JP | 2010-500107 | 1/2010 |
| WO | WO-2004/105831 A2 | 12/2004 |
| WO | WO-2006/019626 A2 | 2/2006 |
| WO | 2008/021025 | 2/2008 |
| WO | 2008/096365 | 8/2008 |
| WO | 2009/149108 | 12/2009 |
| WO | 2010/144483 | 12/2010 |

OTHER PUBLICATIONS

Definition of Adhere by dictionary.com; retrieved from http://dictionary.reference.com/browse/adhere on Apr. 30, 2015.

* cited by examiner

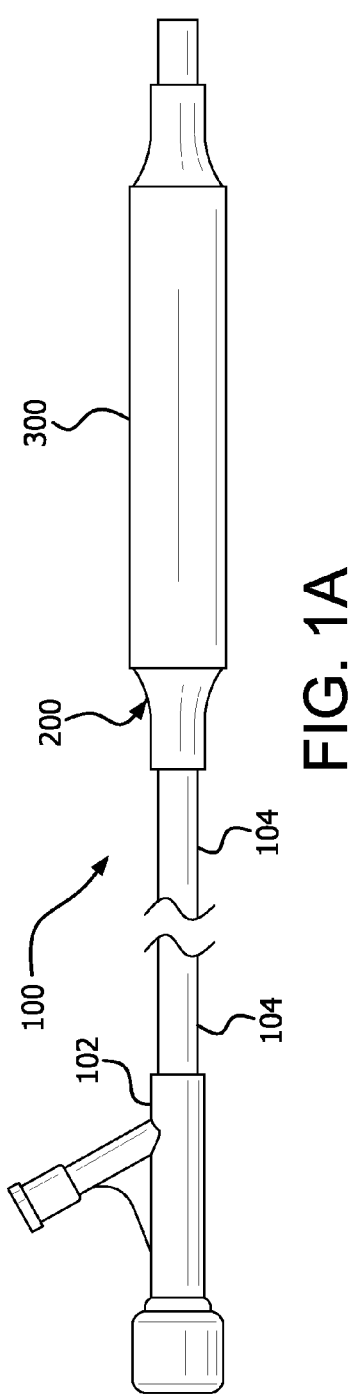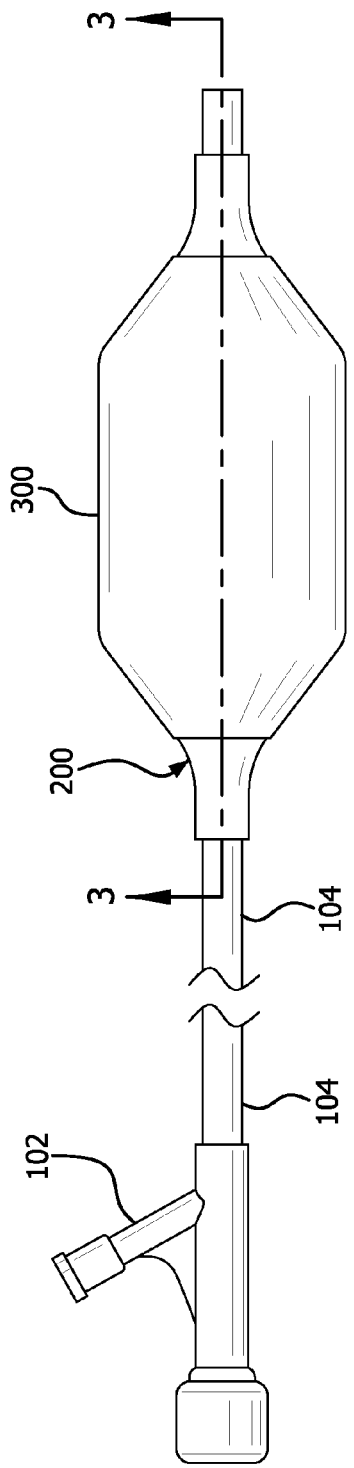

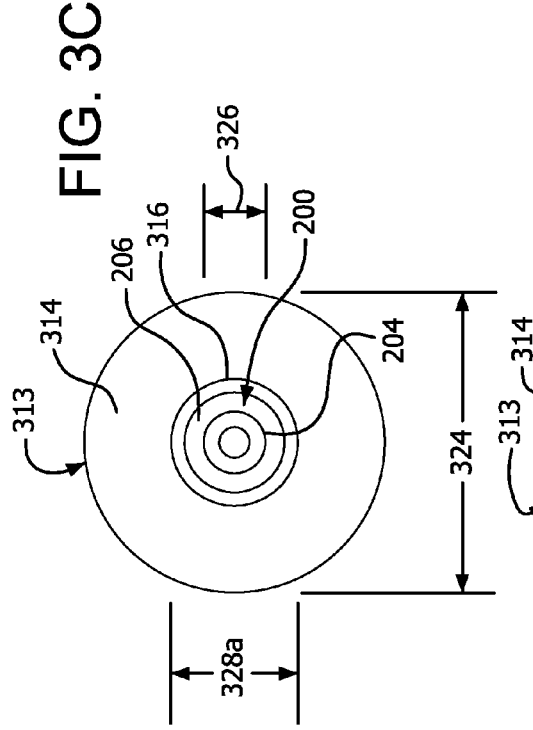
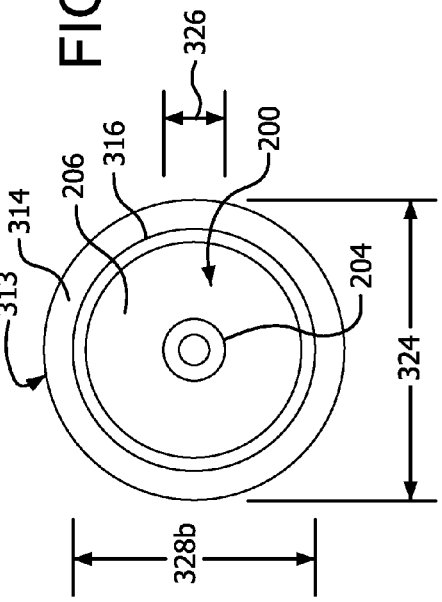
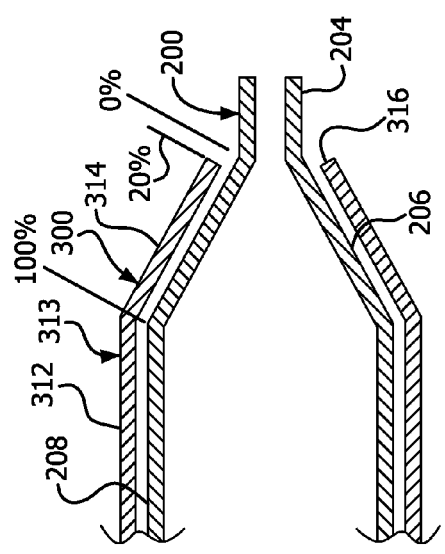
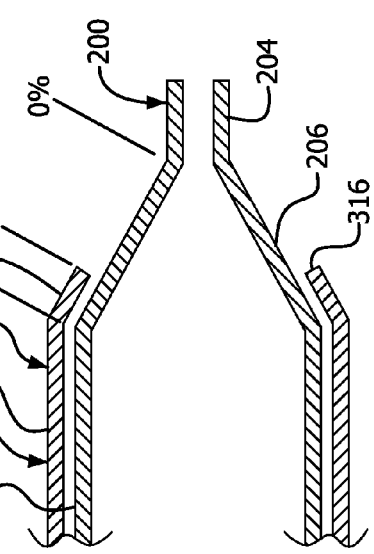
FIG. 3B
FIG. 3C
FIG. 3D
FIG. 3E

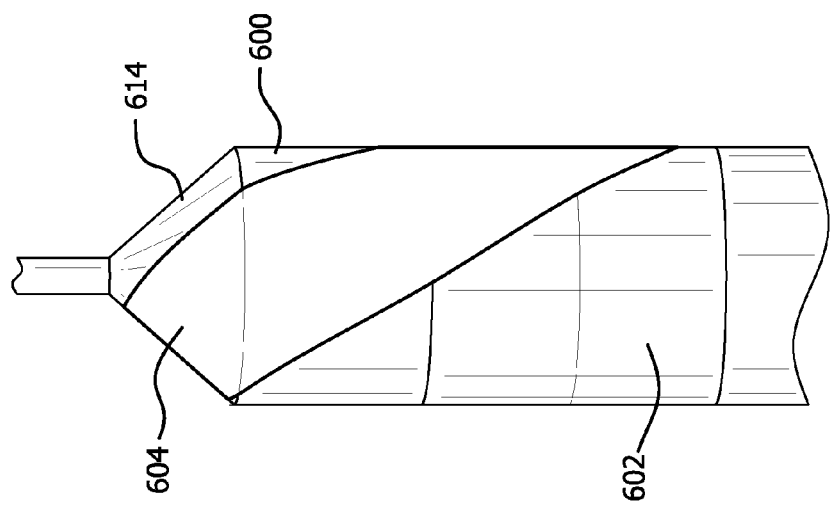
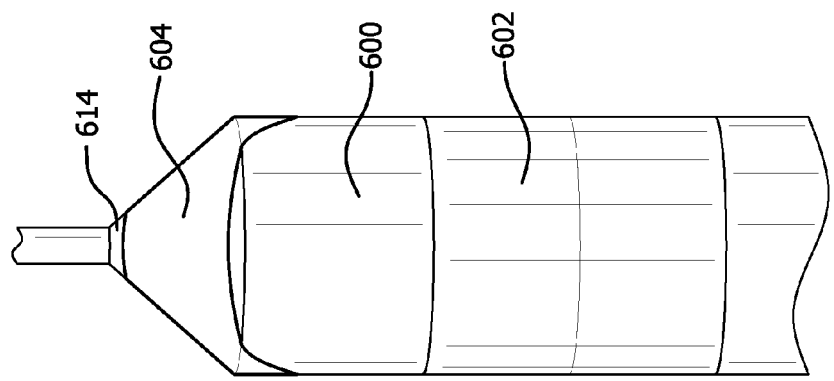

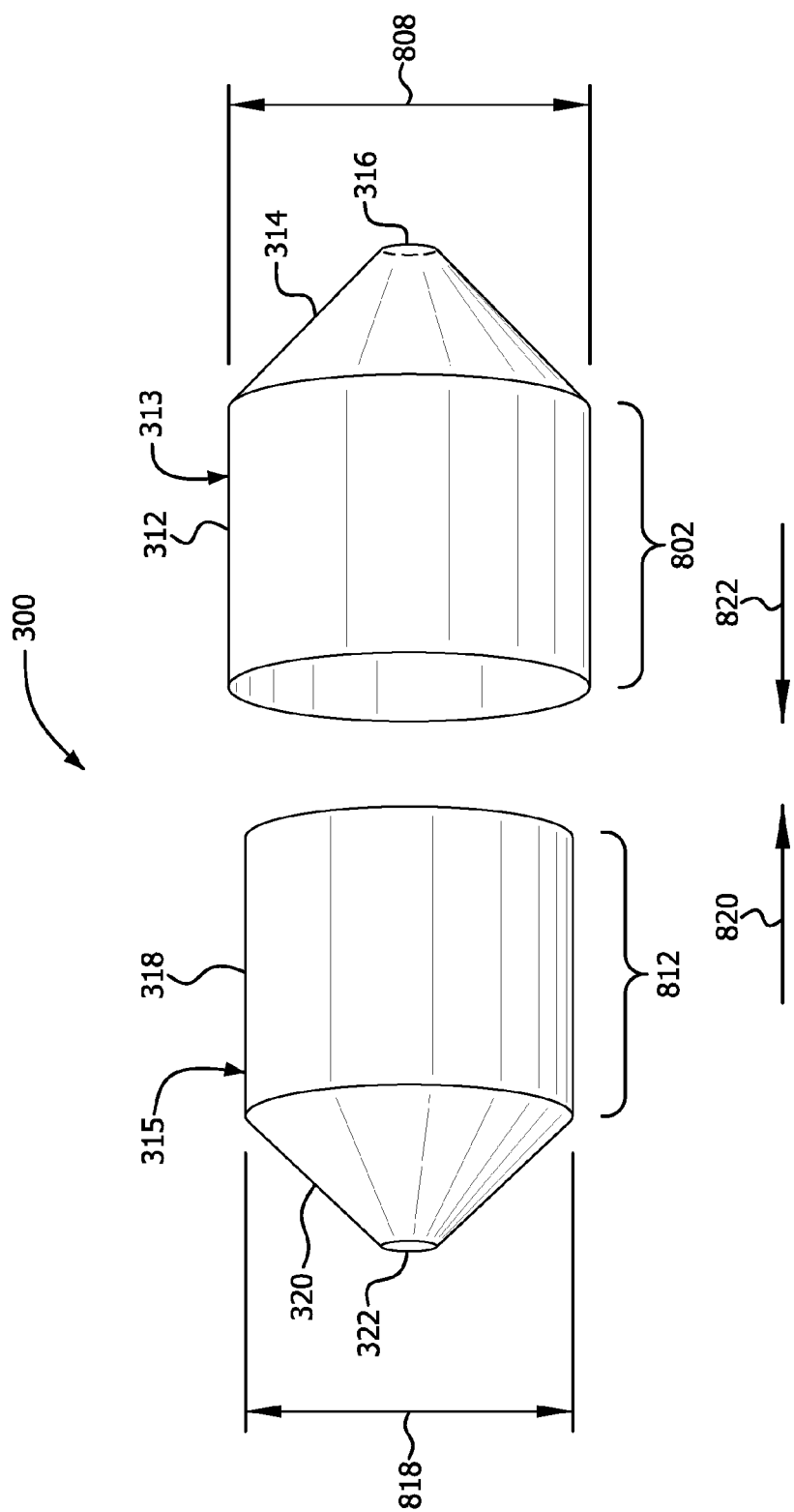

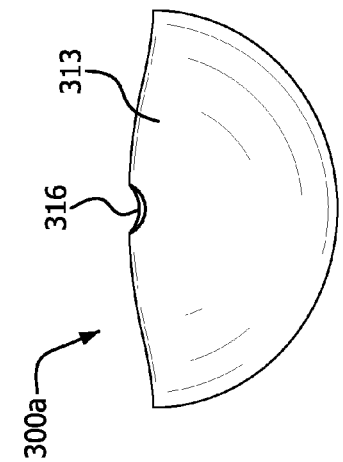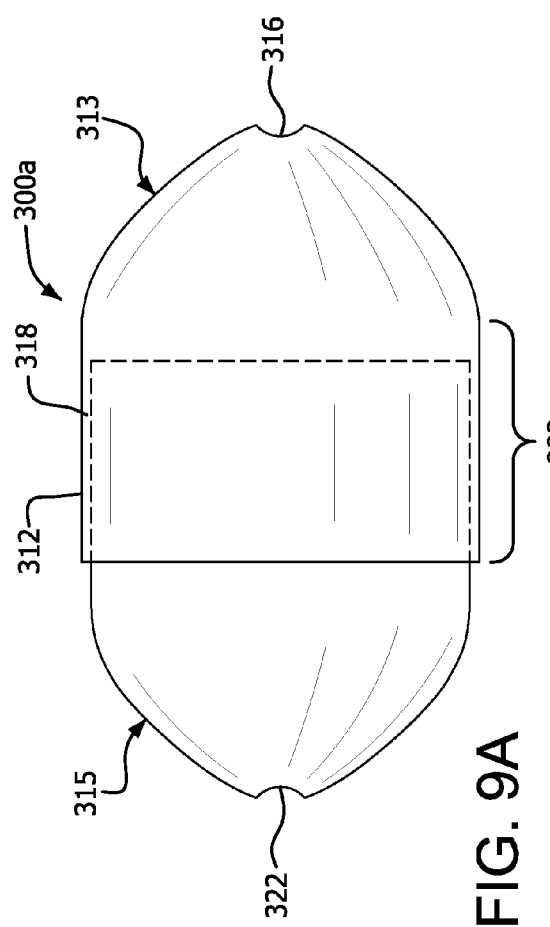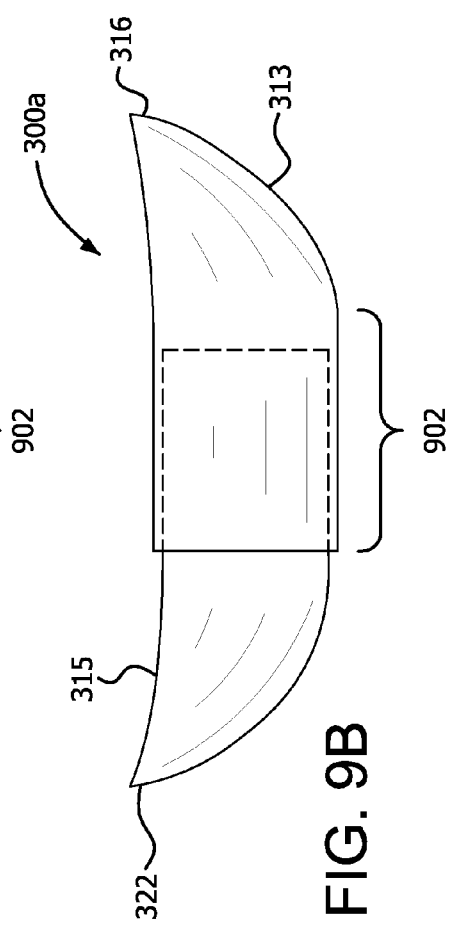

Uncovered Balloon Data *

| Sample | Balloon Size (mm) | Rated Burst Pressure (ATM) | 22 F | 21 F | 20 F | 19 F | 18 F | 17 F | 16 F | 15 F | 14 F | 13 F | 12 F | 11 F |
|---|---|---|---|---|---|---|---|---|---|---|---|---|---|---|
| | | | | | | | | | | | | | | FRENCH SIZE vs. PULL THROUGH FORCE (Lb) |
| 1 | 29x26 | 3.00 | | | | | 2.01 | 1.7 | 1.78 | 2.92 | 2.54 | 3.22 | 4.09 | 4.62 |
| 2 | 29x26 | 3.00 | | | | | 1.89 | 1.82 | 2.27 | 2.73 | 2.38 | 2.92 | 3.37 | 3.71 |
| 3 | 29x26 | 3.00 | | | | | 1.85 | 2.01 | 2.69 | 3.03 | 2.73 | 3.64 | 3.67 | 5.15 |
| 4 | 29x26 | 3.00 | | | | | 1.82 | 1.7 | 2.23 | 2.5 | 2.12 | 2.88 | 3.11 | 3.79 |
| 5 | 29x26 | 3.00 | | | | | 2.08 | 2.42 | 2.31 | 2.92 | 2.46 | 3.83 | 3.33 | 3.6 |
| 6 | 29x26 | 3.00 | | | | | 2.04 | 2.69 | 2.38 | 2.76 | 3.11 | 3.37 | 4.4 | 4.32 |
| 7 | 29x26 | 3.00 | | | | | 2.01 | 1.85 | 2.04 | 2.27 | 2.35 | 3.18 | 4.36 | 4.55 |
| 8 | 29x26 | 3.00 | | | | | 2.54 | 2.5 | 2.8 | 3.3 | 3.49 | 4.24 | 4.32 | 5.12 |
| 9 | 29x26 | 3.00 | | | | | 1.85 | 1.82 | 2.01 | 2.38 | 2.95 | 2.54 | 3.64 | 4.36 |
| 10 | 29x26 | 3.00 | | | | | 1.85 | 2.54 | 2.73 | 2.8 | 2.99 | 3.11 | 3.79 | 4.05 |
| AVERAGE: | | 3.00 | | | | | 1.99 | 2.11 | 2.32 | 2.76 | 2.71 | 3.29 | 3.81 | 4.33 |
| STD. DEV: | | 0.000 | | | | | 0.214 | 0.387 | 0.336 | 0.311 | 0.419 | 0.499 | 0.466 | 0.549 |

Note: The rated burst pressure was 3.00 ATM, the actual burst pressure averaged about 3.2 ATM
* per manufacturer testing

FIG. 11A

| Covered Balloon Data | | FRENCH SIZE vs. PULL THROUGH FORCE (Lb) | | | | | | | | | | | |
|---|---|---|---|---|---|---|---|---|---|---|---|---|---|
| Sample | Balloon Size (mm) | Burst Pressure (ATM) | 22 F | 21 F | 20 F | 19 F | 18 F | 17 F | 16 F | 15 F | 14 F | 13 F | 12 F | 11 F |
| 1 | 29x26 | | 6.12 | | | | | | | | | | | |
| 2 | 29x26 | 9.68 | 5.51 | 3.74 | 4.20 | 3.71 | 3.28 | 5.44 | 4.75 | 5.40 | 7.32 | 7.66 | 11.70 | |
| 3 | 29x26 | 10.73 | 6.41 | 5.07 | 4.35 | 4.48 | 4.91 | 5.21 | 6.25 | 6.57 | 9.31 | 11.50 | | |
| AVERAGE: | | 10.21 | 6.01 | 4.41 | 4.27 | 4.09 | 4.10 | 5.32 | 5.50 | 5.99 | 8.31 | 9.58 | 11.70 | N/A |
| STD. DEV: | | 0.742 | 0.459 | 0.943 | 0.110 | 0.547 | 1.150 | 0.161 | 1.063 | 0.824 | 1.406 | 2.714 | N/A | N/A |

FIG. 11B

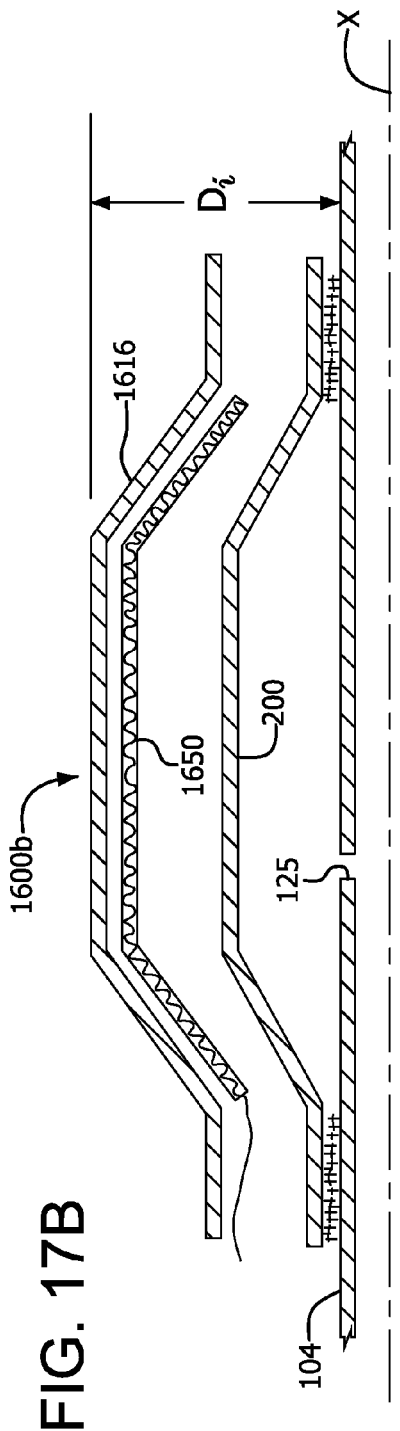
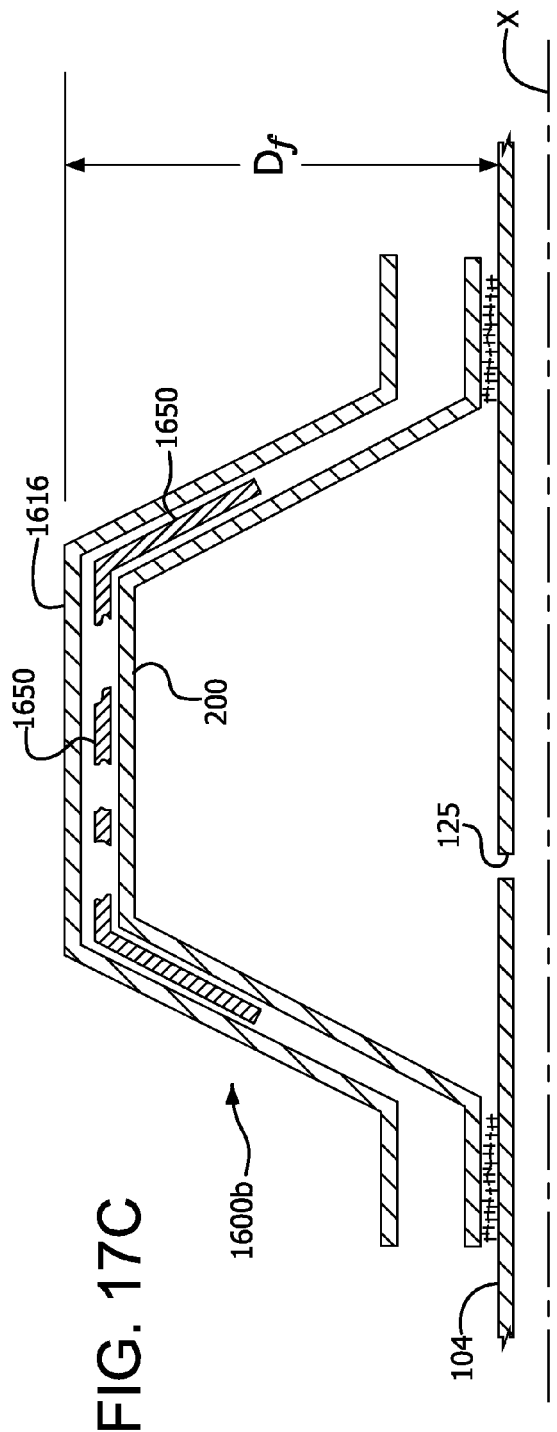

CONTROLLABLE INFLATION PROFILE BALLOON COVER APPARATUS

CROSS REFERENCE TO RELATED APPLICATIONS

This application is a Continuation-In-Part U.S. patent application number 13/529,896 filed Jun. 21, 2012, now U.S. Pat. No. 9,370,643, which claims priority to U.S. Provisional Patent Application number 61/500,555 filed Jun. 23, 2011, and also claims priority to U.S. Provisional Patent Application number 61/535,864 filed Sep. 16, 2011.

FIELD

This disclosure relates generally to a medical device, and more particularly to apparatus and a methods providing a low profile medical balloon with controllable inflation profile.

BACKGROUND

Balloon angioplasty is a widely used procedure for expanding constricted body passageways, such as arteries and other blood vessels. In an angioplasty procedure, an un-inflated balloon attached to a catheter is delivered to a constricted region of a body passageway. Once the balloon is in position at the constricted region, fluid is injected through a lumen of the catheter and into the balloon. The balloon consequently inflates and exerts pressure against the constricted region to expand the passageway. After use, the balloon is collapsed, and the catheter is withdrawn.

Balloons have a number of critical design parameters. One is rated burst pressure, which is the statistically-determined maximum pressure to which a balloon may be inflated without rupturing. In order to expand hard, calcified lesions, it is desirable that the balloon have a relatively high rated burst pressure. It is also desirable that the balloon have a low wall thickness to minimize the profile of the delivery system when the balloon is in a deflated state. For a given balloon material, however, there is a trade-off between burst pressure and wall thickness, in that the burst pressure generally decreases when the wall thickness is reduced.

Accordingly, there is a need for increasing the strength of a balloon to attain a higher rated burst pressure while maintaining a low delivery profile.

Balloons used for stent delivery have the added requirement of delivering a stent in a controlled manner. Balloons with a large difference in their deflated profile (deflated diameter) and their expanded profile (expanded diameter) commonly inflate in an uneven manner along the length of the balloon. By way of example, one end of the balloon may attain an expanded diameter prior to the opposing end, or the middle of the balloon may expand prior to the ends. This inconsistency of inflation increases the likelihood that the stent will be dislodged longitudinally along the length of the balloon moving either partially or fully off the balloon. The inconsistency of inflation profile increases the likelihood for vessel trauma as the stent is unevenly expanded and subsequently unevenly engages the vessel wall.

Accordingly, there is a need in the art for a balloon system that provides for the control of the inflation profile to provide a uniform profile along the length of the balloon as the system is inflated to reduce the risk of stent misalignment/dislodgement and vessel trauma.

Doctors are also commonly faced with a decision pertaining to what diameter stent/balloon system to choose for delivery. Accuracy in measurement technique and the choices in device diameter often limit the doctor's ability to choose a balloon/stent system that is optimally sized for the intended vasculature.

Accordingly, there is a need for a balloon that provides one or more intermediate inflated diameters that are apparent to the doctor during delivery that provides a uniform profile (that is, a relatively uniform diameter) along the length of the balloon at each intermediate diameter.

SUMMARY

An embodiment comprises a catheter balloon having a working length and an expanded and an unexpanded diameter. At least partially surrounding the balloon is a balloon cover having a length and an expanded and unexpanded diameter. Wherein said balloon cover comprises first and second portions, wherein said first and second portions each comprise a working length integrally connected to a taper end having an aperture located at an apex of the taper end and said taper ends of said first and second portions are located at opposite ends of said balloon cover and said first and second working lengths of the first and second cover portions overlap for a substantial portion of the balloon working length.

Another embodiment comprises a balloon cover having a length, an unexpanded and expanded diameter, and first and second portions, wherein said first and second portions each comprise a working length integrally connected to a taper end having an aperture located at an apex of the taper end, and wherein said taper ends of said first and second portions are located at opposite ends of said balloon cover and said first and second working lengths substantially overlap.

Another embodiment comprises a balloon cover having a length, first and second portions, an unexpanded and expanded diameter, and an intermediate section comprising first and second ends, wherein said first and second portions each comprises a working length integrally connected to a taper end having an aperture located at an apex of the taper end, wherein said taper ends of said first and second portions are located at opposite ends of said balloon cover and wherein said first end of said intermediate section overlaps with the working length of said first portion and the second end of said intermediate section overlaps with the working length of said second portion.

Another embodiment comprises a catheter balloon assembly comprising an inflatable balloon having a balloon body portion defining a balloon working length and an un-inflated diameter and a working diameter, and a frangible cover covering at least a portion of the balloon body portion, the frangible cover being operable to rupture under an internal pressure before the rupture of the balloon wherein the frangible balloon cover is operable to control the balloon to open to an intermediate diameter that is less than the working diameter.

Another embodiment comprises a frangible balloon assembly comprising a catheter shaft including an inflation lumen in fluid communication with an inflation port, a balloon coupled to the catheter shaft and in fluid communication with the inflation port, the balloon including a balloon body portion, the balloon having a working diameter, and a frangible cover covering at least a portion of the balloon body portion, the frangible cover being operable to restrain the balloon to an intermediate diameter that is smaller than the working diameter up to a predetermined pressure, the frangible cover operable to rupture at the predetermined pressure to allow the balloon to expand to the working diameter.

Another embodiment comprises a balloon assembly operable to provide a balloon diameter vs. balloon pressure profile generally depicting a balloon inflation sequence providing a first intermediate inflated diameter and final inflated diameter of a balloon such that the balloon attains the first intermediate diameter at a first predetermined pressure, and attains the final diameter at a final predetermined pressure that is lower than the first predetermined pressure.

Another embodiment comprises a balloon assembly operable to provide a balloon diameter vs. balloon pressure profile generally depicting a balloon inflation sequence providing at least one intermediate inflated diameter and a final inflated diameter of a balloon such that the balloon attains the at least one intermediate diameter at a predetermined pressure, and attains the final diameter at a final predetermined pressure that is lower than a predetermined pressure of a last intermediate pressure.

Another embodiment comprises a method of inflating a catheter balloon, comprising providing balloon assembly operable to provide a balloon diameter vs. balloon pressure profile generally depicting a balloon inflation sequence providing at least one intermediate inflated diameter and a final inflated diameter of a balloon such that the balloon attains the at least one intermediate diameter at a predetermined pressure, and attains the final diameter at a final predetermined pressure that is lower than a predetermined pressure of a last intermediate pressure.

BRIEF DESCRIPTION OF THE DRAWINGS

The accompanying drawings are included to provide a further understanding of the embodiments provided herein and are incorporated in and constitute a part of this specification, illustrate embodiments, and together with the description serve to explain the principles of the embodiments.

FIGS. 1A and 1B are top plane views of a balloon catheter and balloon cover, in a deflated and inflated state, respectively, in accordance with an embodiment;

FIGS. 3B and 3C are a partial cross-sectional view and an end view, respectively, of a balloon and a balloon cover having an aperture location relative to a balloon taper portion, in accordance with an embodiment;

FIGS. 3D and 3E are a partial cross-sectional view and an end view, respectively, of a balloon and balloon cover having an aperture location relative to a balloon taper portion different than the embodiment of FIGS. 3B and 3C, in accordance with an embodiment;

FIGS. 6A through 6E are front, right, rear, left and top plane views, respectively, of a mandrel and a film lay-up strap in accordance with an embodiment;

FIG. 8A is a perspective view of a first cover portion and a second cover portion in accordance with an embodiment;

FIGS. 9A through 9C are top, front and right side plane views, respectively, of a folded balloon cover in accordance with an embodiment;

FIGS. 11A and 11B are tabulations of burst and pull through test results for covered and uncovered balloons, respectively, in accordance with embodiments;

FIG. 17B is a side cross-sectional view of a frangible balloon assembly in a state of intermediate inflation wherein the frangible cover is not ruptured and the diameter of the frangible balloon assembly is at an intermediate diameter, in accordance with an embodiment;

FIG. 17C is a side cross-sectional view of a frangible balloon assembly in a state of inflation to the balloon working diameter wherein the frangible cover has ruptured releasing the balloon to attain a final diameter, in accordance with an embodiment;

FIG. 15B is a frangible cover stress strain curve, in accordance with an embodiment.

DETAILED DESCRIPTION OF THE ILLUSTRATED EMBODIMENTS

Figure 2:
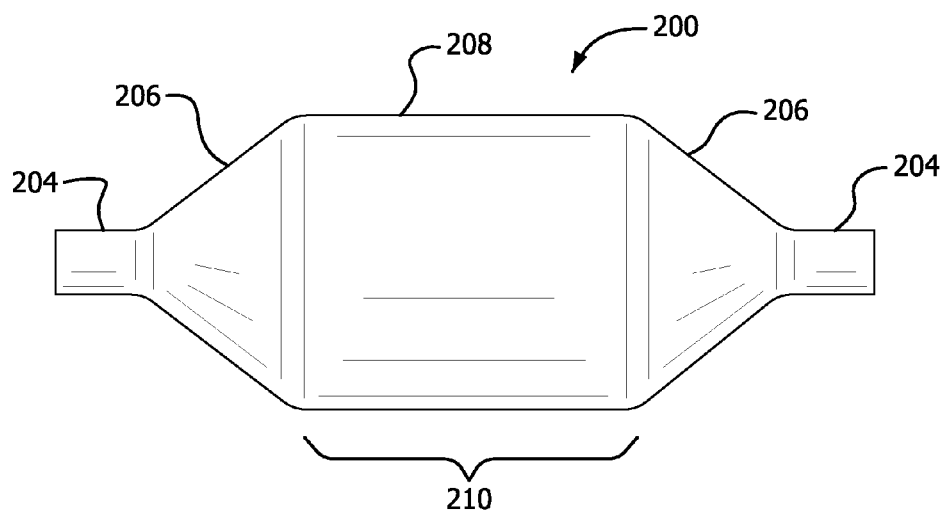
FIG. 2 is a side view of a medical balloon.

It will be apparent to those skilled in the art that various modifications and variations can be made in the embodiment provided herein without departing from the spirit or scope of the invention. Thus, it is intended that the present invention cover the modifications and variations of this invention provided they come within the scope of the appended claims and their equivalents. Although the present invention may be described in connection with various principles and beliefs, the present invention should not be bound by theory.

It should be noted that the accompanying drawing figures referred to herein are not all drawn to scale, but may be exaggerated to illustrate various aspects of the embodiments, and in that regard, the drawing figures should not be construed as limiting.

Described herein is apparatus and methods providing a low profile medical balloon with controllable inflation profile.

As used herein, the term "proximal" relates to a direction that is "closest to the heart", while "distal" relates to a direction that is "furthest from the heart".

FIG. 1A is a side view of a catheter system 100 having a balloon 200 and a balloon cover 300, in accordance with an embodiment. The catheter system 100 further comprises a distal hub 102 and a catheter shaft 104. The balloon 200 is in a deflated state. The balloon cover 300 surrounds a substantial portion of the balloon 200. FIG. 1B is a side view of the catheter system 100 of the embodiment of FIG. 1A with the balloon 200 in an inflated state. The balloon cover 300 surrounds a substantial portion of the inflated balloon 200. Also shown is a cross-sectional plane defined as "3-3" that is referenced in FIGS. 3A, 3B, 3D.

FIG. 2 is a side view of a common medical balloon 200. The balloon 200 comprises two opposed balloon leg portions 204 that are each integrally connected to a balloon taper portion 206, with each of the balloon taper portions 206 connected to a balloon body portion 208 therebetween. A balloon working length 210 is defined as the length of the balloon body portion 208 of the balloon 200 that comprises the approximate length between the opposed balloon taper portions 206. The balloon leg portions 204, balloon taper portions 206, and the balloon body portion 208 define a balloon overall length.

Figure 3A:
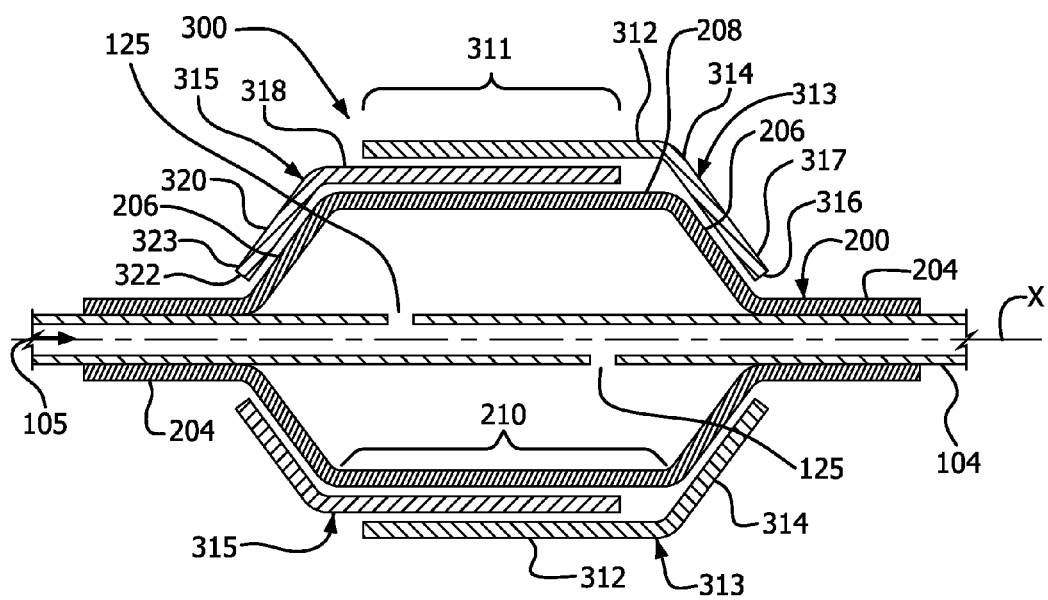
FIG. 3A is a side cross-sectional view of a catheter shaft, a balloon and a balloon cover in accordance with an embodiment.

FIG. 3A is a side cross-sectional view taken along plane 3-3 (see FIG. 1B) showing various elements of the balloon 200 and balloon cover 300 in accordance with an embodiment. Shown is a catheter shaft 104, an inflation lumen 105, and inflation ports 125 with the attached balloon 200. The balloon cover 300 is positioned around the balloon taper portions 206 and the balloon body portion 208 of the balloon 200. The balloon cover 300 comprises a first cover portion 313 and a second cover portion 315. The first cover portion 313 comprises a first cover body portion 312 and a first cover taper portion 314. The first cover body portion 312 is operable to overlay a portion of the balloon body portion 208.

The first cover taper portion 314 is operable to overlay a portion of the balloon taper portion 206 as shown in FIG. 3A. The first cover taper portion 314 defines a first cover aperture 316 located at an apex 317 of the first cover taper portion 314. The first cover aperture 316 is operable to allow the balloon leg portion 204 of the balloon 200 to pass through.

The second cover portion 315 comprises a second cover body portion 318 and a second cover taper portion 320. The second cover body portion 318 is operable to overlay a portion of the balloon body portion 208.

The second cover taper portion 320 is operable to overlay at least a portion of the balloon taper portion 206 as shown in FIG. 3A. The second cover taper portion 320 defines a second cover aperture 322 located at an apex 323 of the second cover taper portion 320. The second cover aperture 322 is operable to allow the balloon leg portion 204 of the balloon 200 to pass through.

Referring again to FIG. 3A, the first cover taper portion 314 and the second cover taper portion 320 are located at opposite ends of the balloon cover 300. The first cover portion 313 and the second cover portion 315 are coaxially aligned along axis X and overlay the balloon 200 such that at least a portion of the first cover body portion 312 overlays at least a portion of the second cover body portion 318. The overlay of the first cover body portion 312 and the second cover body portion 318 defines a cover working length 311. In the embodiment of FIG. 3A, the working length 311 overlays a substantial portion of the balloon working length 310. A "substantial portion of the balloon working length" is defined herein as about over 50% to about 100% of the balloon working length. In embodiments, a "substantial portion of the balloon working length" comprises over and/or about 60%, about 70%, about 80%, about 90%, about 95%, and about 98% of the balloon working length 210.

Shown in FIG. 3B is a partial cross-sectional side view of the first cover portion 313 of the balloon cover 300, shown overlaying an inflated balloon 200. The additional layers shown in FIG. 3A have been omitted for clarity. The aperture 316 is shown positioned about 20% "up along" the balloon taper portion 206 of the balloon 200. As shown, a position that is "zero %" up the balloon taper portion 206 is located at a junction of the balloon leg 204 and the balloon taper portion 206. A position that is "100%" up the balloon taper portion 206 is located at the junction of the balloon taper portion 206 and the balloon body portion 208. FIG. 3C is an end view of the balloon 200 and a first cover portion 313. Shown is the cover aperture 316 positioned about 20% up the balloon taper portion 206 of the balloon 200. Also shown are inflated balloon diameter 324, balloon leg diameter 326 and aperture diameter 328a. The position of the aperture 316 relative to the balloon taper portion 206 of the balloon 200 can be expressed as a ratio of aperture diameter 328a to the inflated balloon diameter 324. Similarly, the position of the aperture 316 relative to the balloon taper portion 206 can be expressed as a ratio of aperture diameter 328a to the balloon leg portion diameter 326.

FIGS. 3D and 3E are similar to previous FIGS. 3B and 3C. As shown in FIG. 3D, the aperture 316 is shown positioned about 75% "up along" the balloon taper portion 206 of the balloon 200. FIG. 3E is an end view of the balloon 200 with the surrounding first cover portion 313. Shown is an aperture 316 positioned about 75% up the balloon taper portion 206 of the underlying balloon 200. Also shown are inflated balloon diameter 324, leg portion diameter 326 and aperture diameter 328b. The position of the aperture 316 relative to the balloon taper portion 206 can be expressed as a ratio of aperture diameter 323b to the inflated balloon diameter 324. Similarly, the position of the aperture 316 relative to the balloon taper portion 206 can be expressed as a ratio of aperture diameter 328b to the leg portion diameter 326. Note that FIGS. 3C and E are not drawn to scale, but are intended to illustrate a difference in the size of the aperture 316.

Large aperture sizes may useful for many applications including, but not limited to, for designing a balloon fail safe so that the balloon 200 will fail only in the area not covered by the balloon cover 300, such as the balloon taper portion 206 area of the balloon (see FIG. 2) and/or for reducing pull through forces (see below) by reducing the amount of material in the balloon taper portion 206 and thus reducing profile in that area.

Endoluminal balloons are typically blow molded from a uniform wall thickness tube. Once molded, the tube is stretched resulting in a varying wall thickness along the length of the balloon. The balloon is commonly thickest at the balloon leg portions 204 and becomes progressively thinner along the balloon taper portion 206 and the thinnest at the balloon body portion 208. Thickness is inverse to the stress on the balloon while under pressure. The thinnest wall of the blow molded balloon, for example, will therefore be under the greatest stress when inflated.

The balloon leg portions 204 substantially retain the thickness of the uniform wall thickness tube before blow molding the balloon body portion and the balloon taper portions and thus are commonly a wall thickness that is oversized for the stresses that the leg portions are likely to experience when the balloon 200 is inflated. This extra thickness and thus the profile may increase the minimum introducer size that a balloon may be withdrawn.

The balloon covers 300 in accordance with embodiments provided herein, cover, and therefore reinforce, the thinner portions of the balloon 200. Thus, in accordance with embodiments, a balloon cover 300 provides additional strength to the balloon 200. In accordance with an embodiment, the thinnest part of the balloon 200 is covered by a strongest portion of the balloon cover 300 and vice versa. Embodiments of a balloon cover 300 increases the rated burst pressure of a balloon 200 with minimal addition to withdrawal profile.

Balloons and balloon covers may be fabricated from a variety of commonly known materials such as Amorphous Commodity Thermoplastics that include Polymethyl Methacrylate (PMMA or Acrylic), Polystyrene (PS), Acrylonitrile Butadiene Styrene (ABS), Polyvinyl Chloride (PVC), Modified Polyethylene Terephthalate Glycol (PETG), Cellulose Acetate Butyrate (CAB); Semi-Crystalline Commodity Plastics that include Polyethylene (PE), High Density Polyethylene (HDPE), Low Density Polyethylene (LDPE or LLDPE), Polypropylene (PP), Polymethylpentene (PMP); Amorphous Engineering Thermoplastics that include Polycarbonate (PC), Polyphenylene Oxide (PPO), Modified Polyphenylene Oxide (Mod PPO), Polyphenelyne Ether (PPE), Modified Polyphenelyne Ether (Mod PPE), Thermoplastic Polyurethane (TPU); Semi-Crystalline Engineering Thermoplastics that include Polyamide (PA or Nylon), Polyoxymethylene (POM or Acetal), Polyethylene Terephthalate (PET, Thermoplastic Polyester), Polybutylene Terephthalate (PBT, Thermoplastic Polyester), Ultra High Molecular Weight Polyethylene (UHMW-PE); High Performance Thermoplastics that include Polyimide (PI, Imidized Plastic), Polyamide Imide (PAI, Imidized Plastic), Polybenzimidazole (PBI, Imidized Plastic); Amorphous High Performance Thermoplastics that include Polysulfone (PSU), Polyetherimide (PEI), Polyether Sulfone (PES), Polyaryl Sulfone (PAS); Semi-Crystalline High Performance Thermoplastics that include Polyphenylene Sulfide (PPS), Polyetheretherketone (PEEK); and Semi-Crystalline High Performance Thermoplastics, Fluoropolymers that include Fluorinated Ethylene Propylene (FEP), Ethylene Chlorotrifluroethylene (ECTFE), Ethylene, Ethylene Tetrafluoroethylene (ETFE), Polychlortrifluoroethylene (PCTFE), Polytetrafluoroethylene (PTFE), Polyvinylidene Fluoride (PVDF), Perfluoroalkoxy (PFA). Other commonly known medical grade materials include elastomeric organosilicon polymers, polyether block amide or thermoplastic copolyether (PEBAX).

Balloon covers in accordance with embodiments can be fabricated by a variety of methods such as molding, vacuum/pressure forming, film-wrapping, film-layering, fiber winding or other methods known in the art.

The following describes an embodiment of a method of making a balloon cover utilizing thin, polymeric film lay-ups that can be used to fabricate various balloon covers in accordance with embodiments presented herein. In accordance with an embodiment, a method comprises the following steps.

Figure 4:
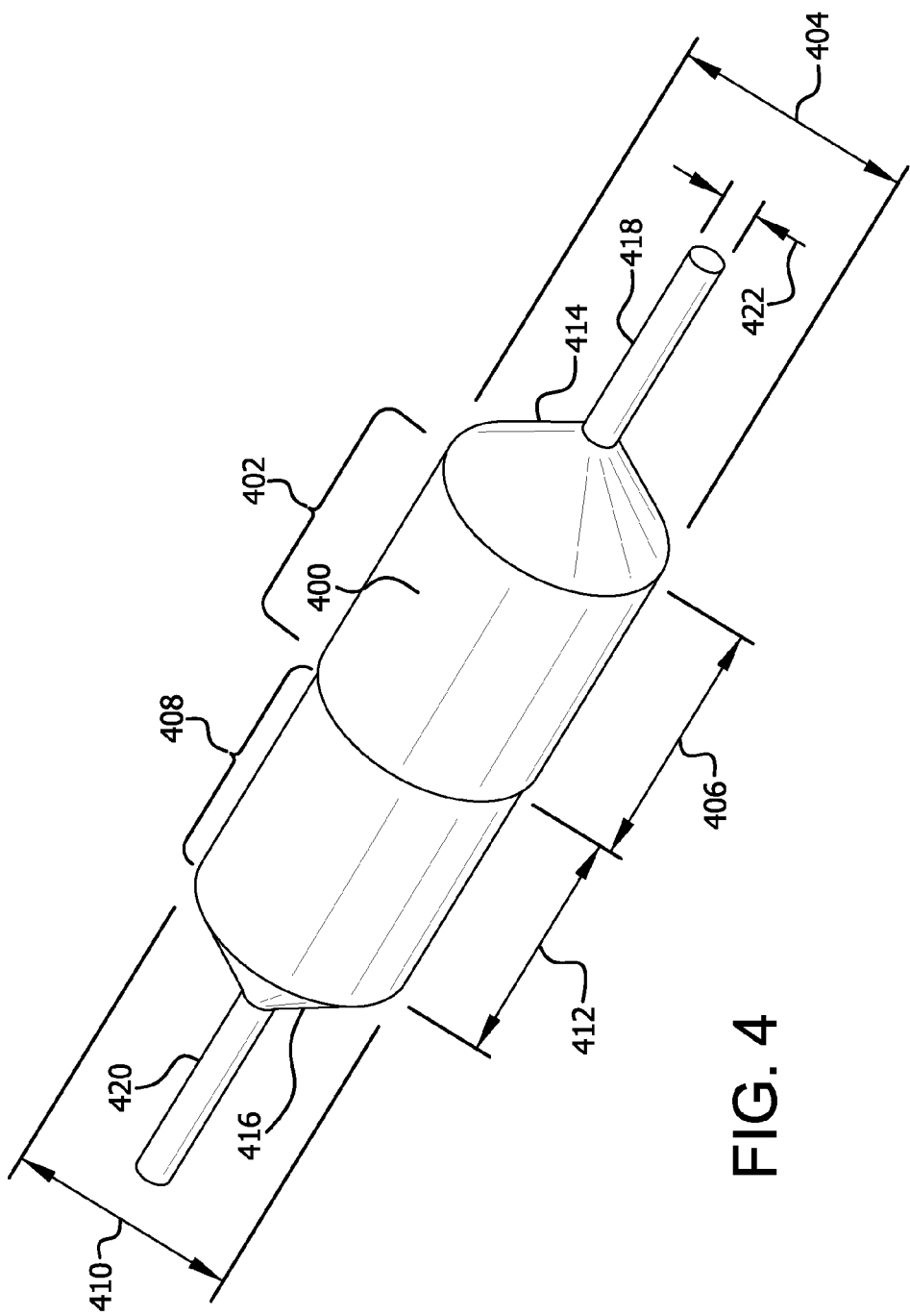
FIG. 4 is a perspective view of a mandrel used to form balloon cover portions in accordance with an embodiment.

Fabricate a stepped metallic, film lay-up mandrel fabricated according to FIG. 4. Shown is a metallic mandrel 400 having a first cylindrical portion 402. The first cylindrical portion 402 has a diameter 404 and a length 406. Similarly, the metallic mandrel 400 has a second cylindrical portion 408. The second cylindrical portion 408 has a diameter 410 and a length 412. The first and second cylindrical portions 402, 408 are integrally connected to opposing taper portions (414, 416). The opposing taper portions (414, 416) are integrally connected to opposing shafts (418, 420), having diameters 422. The lengths (406, 412), diameters (404, 410) and taper portion (414, 416) dimensions can be tailored to accommodate the dimensions of a subsequent underlying balloon. Lengths (406, 412) can range from about 1 mm to more than 100 mm, diameters (404, 410) can range from about 1 mm to more than 100 mm and taper portion angles can range from about 10° to about 90°. In one embodiment, the cover diameter is undersized by about at least 5% relative to the balloon diameter. Undersizing the balloon cover by at least 5% allows the balloon cover to bear the radial load of an inflated balloon, thus not allowing the balloon to fail, at least in the covered region of the balloon.

Using the mandrel 400 to form a first cover portion and a second cover portion having overlapping cover body portions defining a working length. For the cover body portions to overlap, a first cover portion is fabricated to have a cover body portion inner diameter that is slightly larger than the cover body portion outer diameter of the second cover portion. The difference between the cover body portion diameters is dictated by the different diameters of the first cylindrical portion 402 and the second cylindrical portion

408. For example diameter 404 can be about 0.012" larger than diameter 410, accommodating balloon covers with a 0.006" wall thickness.

Figure 5:
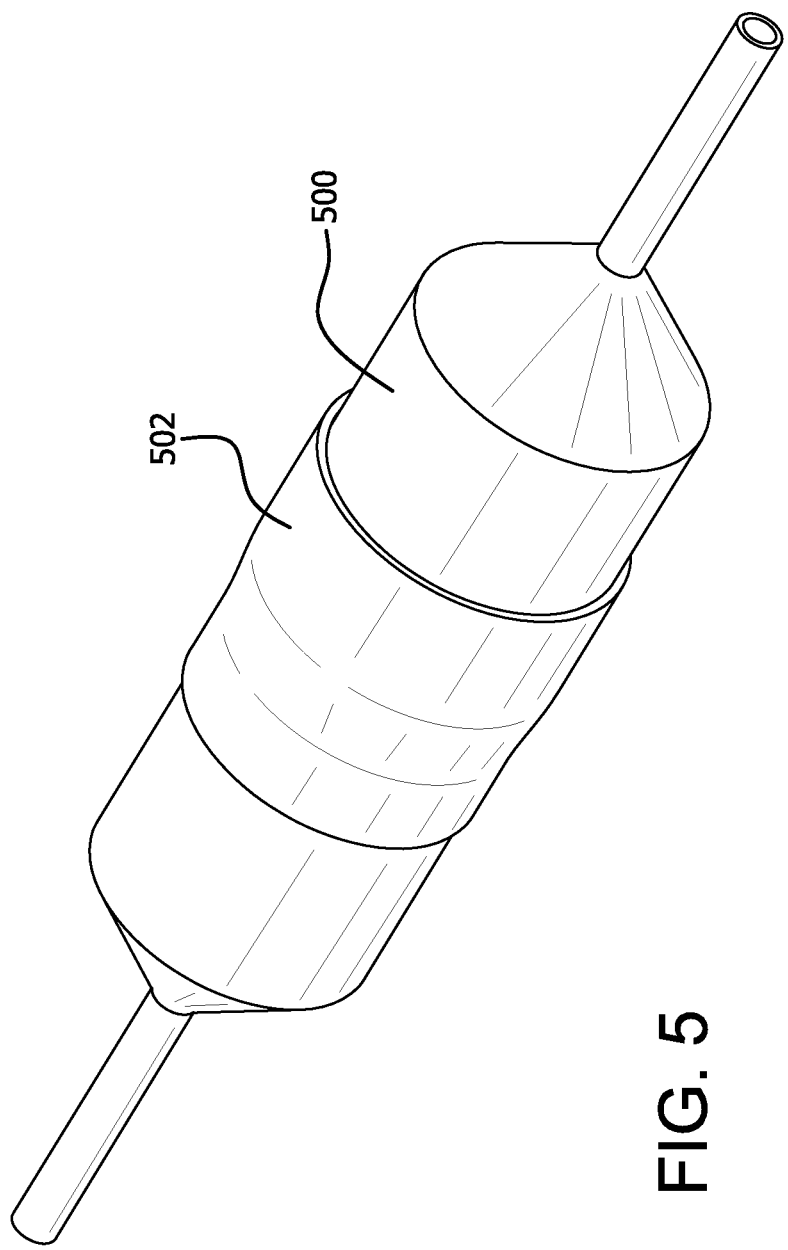
FIG. 5 is a perspective view of a mandrel used to form balloon cover portions further showing a manufacturing aid in accordance with an embodiment.

Mount one of the shafts (418, 420) onto a rotatable collet to hold the mandrel and allow rotation of the mandrel during subsequent processing steps. As shown in FIG. 5, a manufacturing aid, in the form of a film 502 coated with a thermoplastic adhesive can be added to the center portion of the mandrel 500. For example, two to five circumferential wraps can be applied. The layers can be secured by reflowing the thermoplastic adhesive by the application of heat, such as by a soldering iron or other heating means. The width of the film and the location on the mandrel can be selected to accommodate the dimensions of desired balloon cover portions. A suitable film can comprise expanded polytetrafluoroethylene (ePTFE) imbibed or coated with a thermoplastic fluoroelastomer or other combinations of polymeric films and thermoplastics.

Figure 6B:
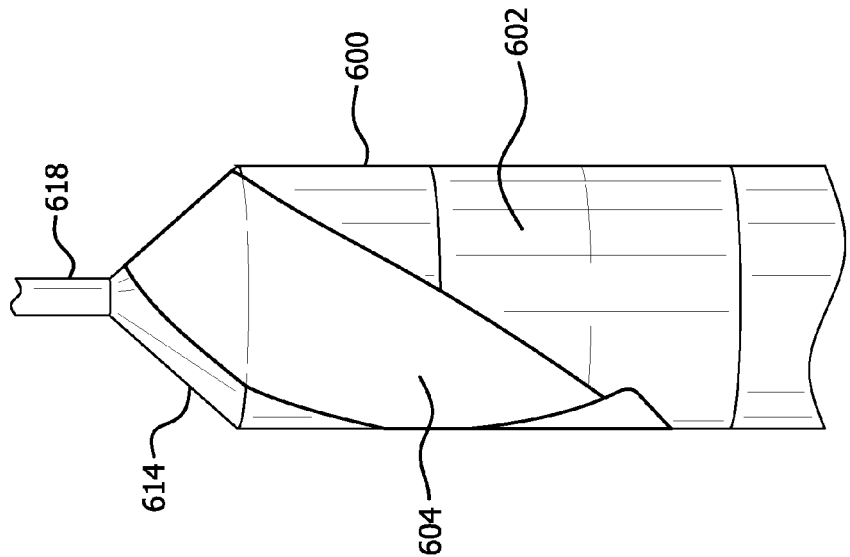
Figure 6A:
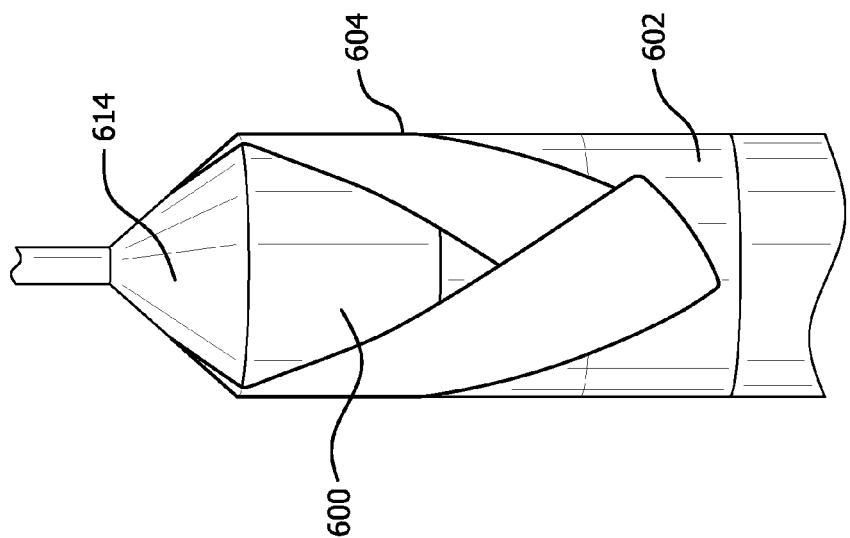

Apply a series of film layers or straps, as described in FIGS. 6A through 6E, onto the first cylindrical portion (larger diameter relative to the second cylindrical portion) and onto the integrally connected taper portion of the mandrel. Shown in FIG. 6A is a front plane view of a mandrel 600 with a strap of a thin polymeric film 604 positioned over a taper portion 614. Shown in FIG. 6B is a right side plane view (of FIG. 6A) of a mandrel 600 with a strap of a thin polymeric film 604 positioned over a taper portion 614. As shown, the film strap 604 is closely abutted against the base of the integral shaft 618. Similarly, FIG. 6C is a rear side plane view (of FIG. 6A) of a mandrel 600 with a strap of a thin polymeric film 604 positioned over a taper portion 614. FIG. 6D is a left side plane view (of FIG. 6A) of a mandrel 600 with a strap of a thin polymeric film 604 positioned over a taper portion 614. Note that the width and size of the straps can vary depending on the application.

Smooth out and heat tack the portions of the film strap 604 to the overlying film/thermoplastic manufacturing aid 602, resulting in one film strap formed onto the mandrel 600.

Figure 6E:
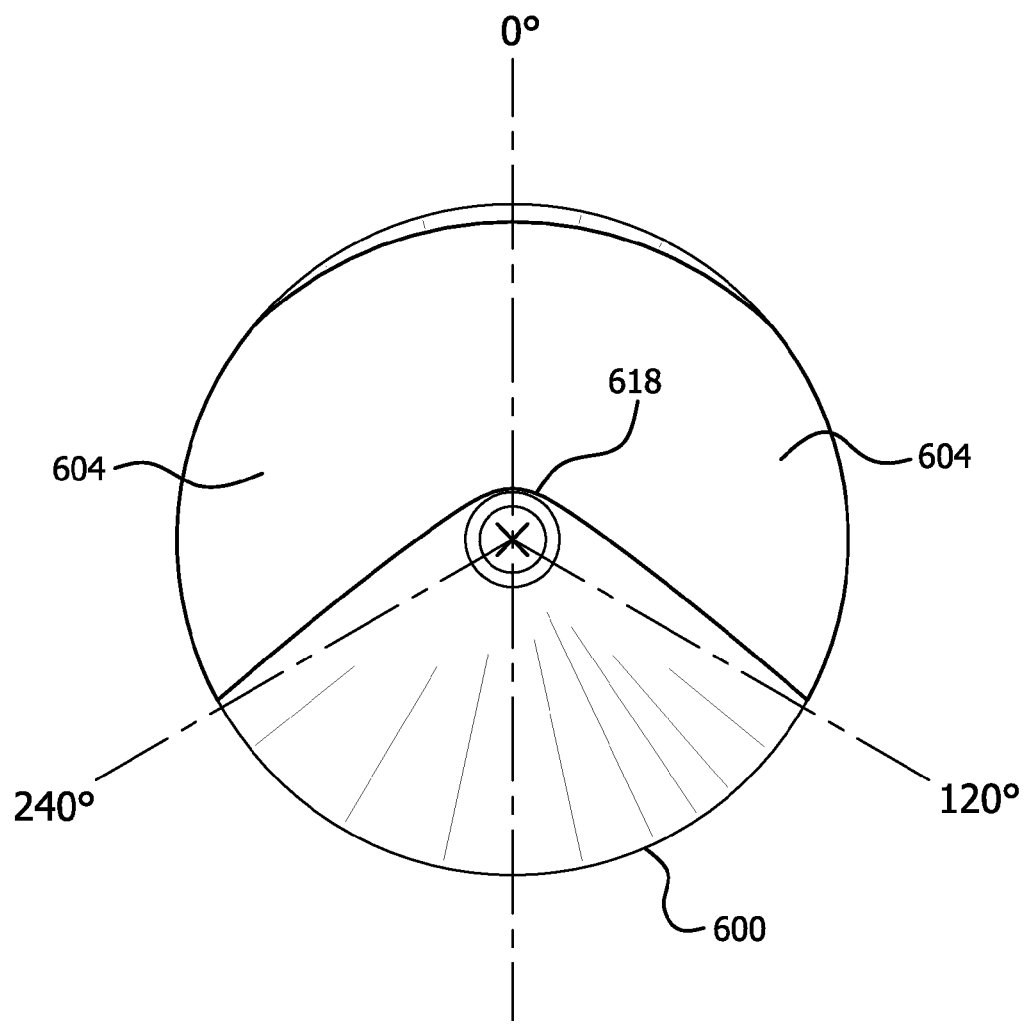

FIG. 6E is a top plane view (of FIG. 6A) showing the film 604 closely abutted against the integral shaft 618. For reference, the film shown is oriented (relative to the mandrel 600) at a "zero degree" position. Two additional film straps can be added in a "clocked" fashion whereby the point where the film strap abuts the integral shaft 618 is oriented about 120° relative to the previous film strap. The two additional film straps can be heat tacked to the manufacturing aid 602 resulting in three film straps formed onto the mandrel 600.

The polymeric film used as a film strap can comprise an expanded polytetrafluoroethylene (ePTFE) film coated on one side with a thermoplastic (or thermoset) adhesive. The three film straps of FIGS. 6A through 6E can have the adhesive side oriented out and away from the mandrel.

EPTFE may be made as taught by U.S. Pat. Nos. 3,953,566 and 4,187,390, both of which are incorporated by reference herein. In another embodiment, said ePTFE is impregnated with a thermoplastic (or thermoset) adhesive, silicone adhesive, silicone elastomer, silicone dispersion, polyurethane or another suitable elastomeric material. Impregnation involves at least partially filling the pores of the porous PTFE. U.S. Pat. No. 5,519,172 teaches in detail the impregnation of porous PTFE with elastomers, such as the one taught in U.S. Pat. No. 7,462,675. In an embodiment, the film comprises an elastomer so that when formed into a balloon cover in accordance with an embodiment, the cover will expand and contract, thus also contracting and/or refolding the balloon.

Figure 7A:
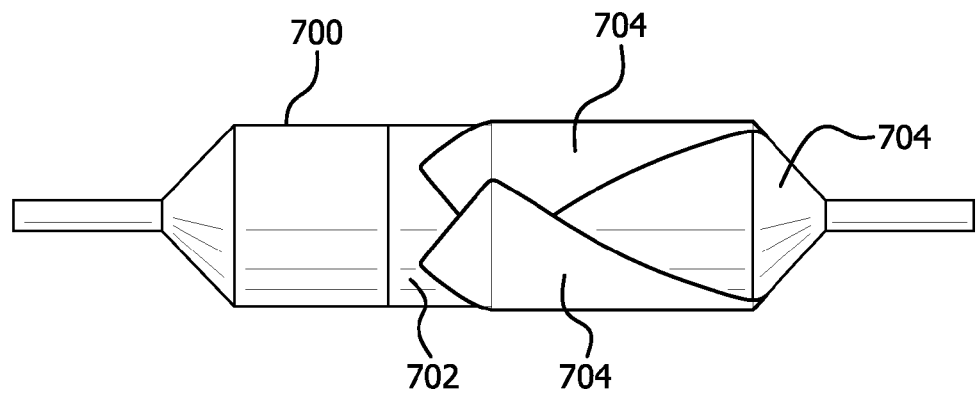
FIGS. 7A and 7B are top plane views, respectively, of a mandrel with film lay-up straps and an additional radial film layer in accordance with an embodiment.
Figure 7B:
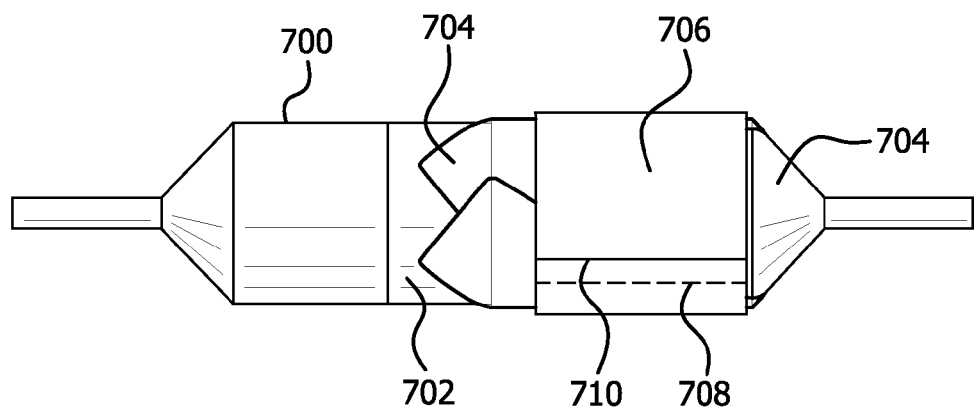

A circumferentially wrapped film layer can be added to the wrapped mandrel. Shown in FIG. 7A, a mandrel 700 having a wrapped film manufacturing aid 702 and three polymeric film straps 704 are wrapped. As shown in FIG. 7B, a film layer 706 can be circumferentially wrapped about the first cylindrical portion (FIG. 4, 402). The circumferentially wrapped film layer 706 can have an end-to-end (708, 710) overlap as shown. The polymeric film used as a circumferential wrap 706 can comprise an ePTFE film, coated on one side with a thermoplastic (or thermoset) adhesive. The circumferential wrap 706 can have the adhesive side oriented out and away from the mandrel. The overlapping ends of the film can be heat tacked and bonded together.

Three additional film straps can be added to the first cylindrical portion (FIG. 4, 402). The first additional film strap can be added in "clocked" fashion whereby the point where the film strap abuts the integral shaft 618 (FIG. 6) is oriented about 60° relative to the previous film strap. The second and third additional film straps can then be added in a "clocked" fashion whereby the point where the film strap abuts the integral shaft 618 (FIG. 6) is oriented about 120° relative to the previous film strap.

The portions of the film straps overlying the film/thermoplastic manufacturing aid 602 (FIG. 6) can be smoothed out and heat tacked to the manufacturing aid.

The polymeric film used as a film strap can comprise an ePTFE film, coated on one side with a thermoplastic (or thermoset) adhesive. The three additional film straps can have the adhesive side oriented inward and towards the mandrel.

A circumferentially wrapped film layer can be added to the wrapped mandrel. The polymeric film used as a circumferential wrap can comprise an ePTFE film coated on one side with a thermoplastic (or thermoset) adhesive. The circumferential wrap can have the adhesive side oriented inward and towards the mandrel.

Using a process as similar to that described in FIGS. 6A through 6E, a series of film layers or straps can be applied onto the second cylindrical portion (smaller diameter relative to the first cylindrical portion) and onto the integrally connected taper portion of the mandrel.

Six film straps can be applied according to the process described above. The adhesive side of the film straps can be oriented out and away from the mandrel.

Two layers of a circumferentially wrapped film can be added to the wrapped mandrel. The circumferentially wrapped film can be applied according to the process described above and can have the adhesive side of the film straps oriented out and away from the mandrel.

The mandrel with film wrapped first and second cylindrical portions and integrally connected taper portions can then be heat treated in an air convection (e.g. in an over set of 250° C. for about 30 minutes). The heat treatment reflows the thermoplastic adhesive and bonds the various film layers together. The mandrel and films can then be ambient, forced air cooled for about 30 minutes.

The bonded films on the first and second cylindrical portions and integrally connected taper portions can then be circumferentially cut and removed from the mandrel. The location of the circumferential cut can determine the desired first cover body portion and the second cover body portion of the first cover portion and the second cover portion, respectively. FIG. 8A is a side perspective view of a balloon cover 300 comprising a larger diameter first cover portion 313 having a first cover body portion 312 integrally connected to a first cover taper portion 314. The first cover taper portion 314 has an aperture 316 located at an apex of the first cover taper portion 314. Also shown in FIG. 8A is a smaller diameter second cover portion 315 having a second cover body portion 318 integrally connected to a second cover taper portion 320. The second cover taper portion 320 has an aperture 322 located at an apex of the second cover taper portion 320.

As further shown in FIG. 8A, the second cover portion 315 can be inserted into the first cover portion 313 by translating the second and first cover portions as indicated by direction arrows (820, 822), so that the first cover body portion 312 and the second cover body portion 318 are substantially overlapped. "Substantially overlapped" is defined herein as an overlap of the first and second cover body portions of about over 50% to about 100%. In accordance with embodiments, "substantially overlapped" comprises about 60%, about 70%, about 80%, about 90%, about 95%, about 98% of the first and second cover body portions defining the cover working length.

Figure 8B:
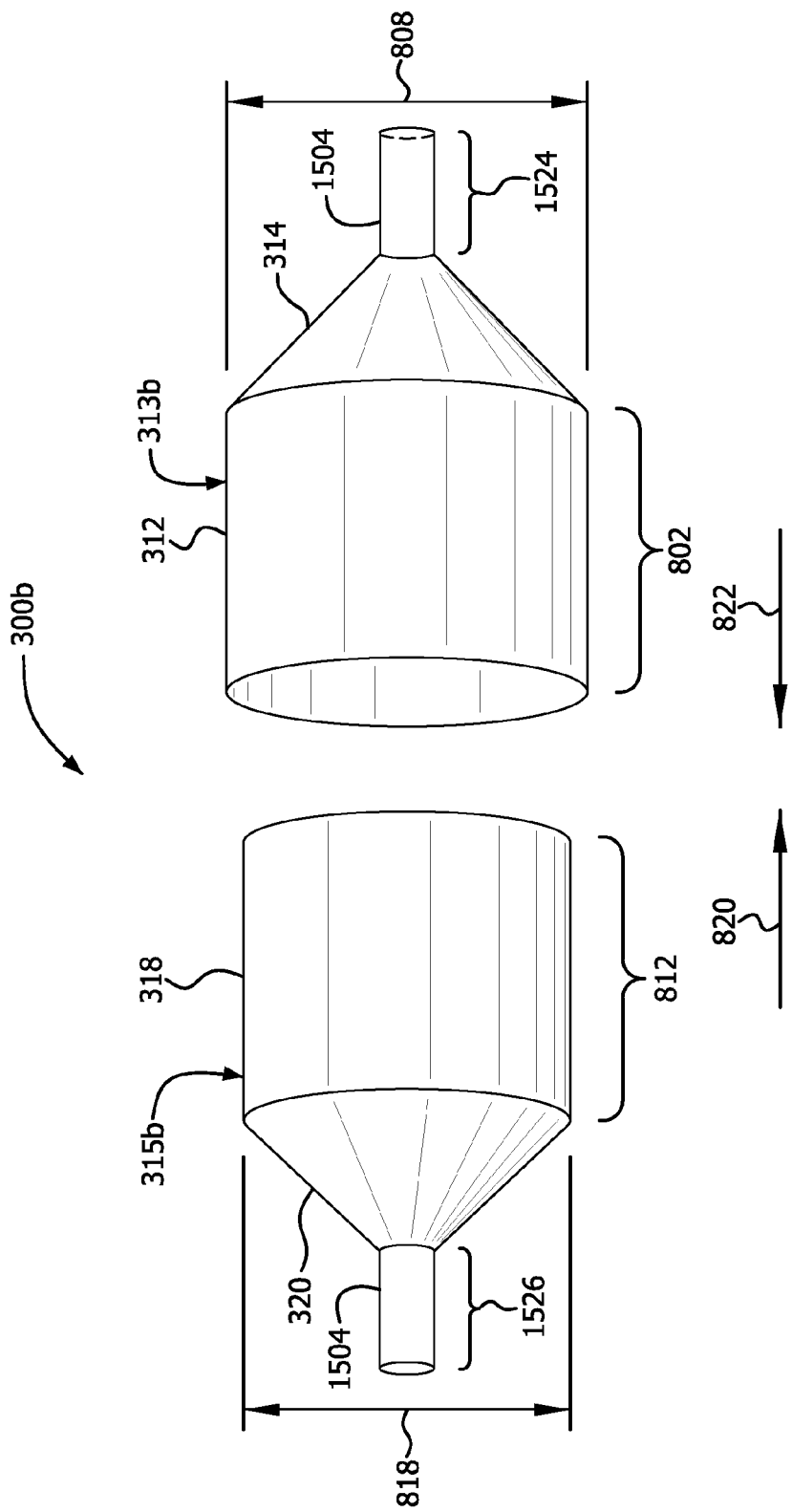
FIG. 8B is a perspective view of a first legged cover portion and a second legged cover portion in accordance with an embodiment.

In accordance with another embodiment, the balloon cover may further comprise a leg portion extending from each of the cover taper portions. The leg portions are operable for receiving therein balloon leg portions 204 shown in FIG. 2, for example. FIG. 8B is a side perspective view of a legged balloon cover 300b comprising a first legged cover portion 313b and a second legged cover portion 315b. The first legged cover portion 313b includes a first cover body portion 312 integrally connected to a first cover taper portion 314, further comprising a cover leg portion 1504 located at an apex of the first cover taper portion 314. The second legged cover portion 315b includes a second cover body portion 318 integrally connected to a second cover taper portion 320, further comprising a cover leg portion 1504 located at an apex of the second cover taper portion 320.

In preparation for bonding the first cover body portion 312 and second the cover body portion 318 together, the first cover portion 313 and second cover portion 315 are flattened-out to form a cup-shaped assembly 300a as generally depicted in FIGS. 9A through 9C. FIG. 9A is a top plane view of flattened first cover portion 313 and second cover portion 315 after having been assembled such that the second cover body portion 318 is overlapped by the first cover body portion 312 to the desired amount defining the working length 902. As shown in FIG. 9A, the second cover body portion 318 is substantially overlapped by the first cover body portion 312. Also shown are apertures 316,322 located at apexes of the cover taper portions of the first cover portion 313 and second cover portion 315. FIG. 9B is a front plane view of the cup-shaped assembly shown in FIG. 9A, while FIG. 9C is a right side plane view of the cup-shaped assembly 300a shown in FIG. 9A.

Figure 10A:
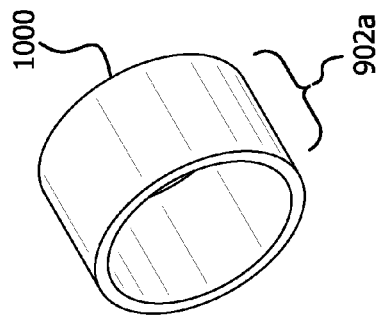
FIGS. 10A through 10C are perspective, front and right plane views, respectively, of a folded balloon cover, depicting a bonding process, in accordance with an embodiment.
Figure 10C:
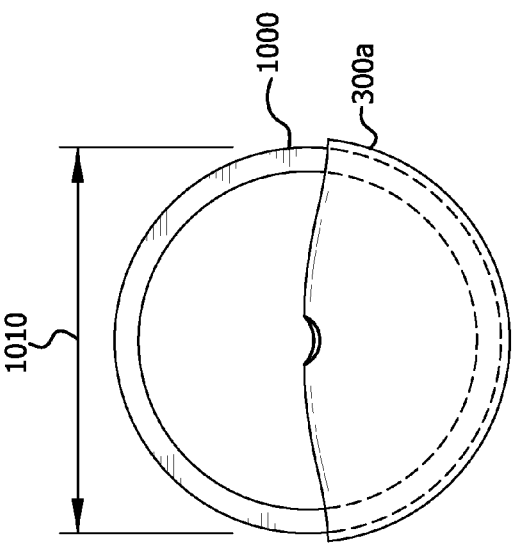
Figure 10B:
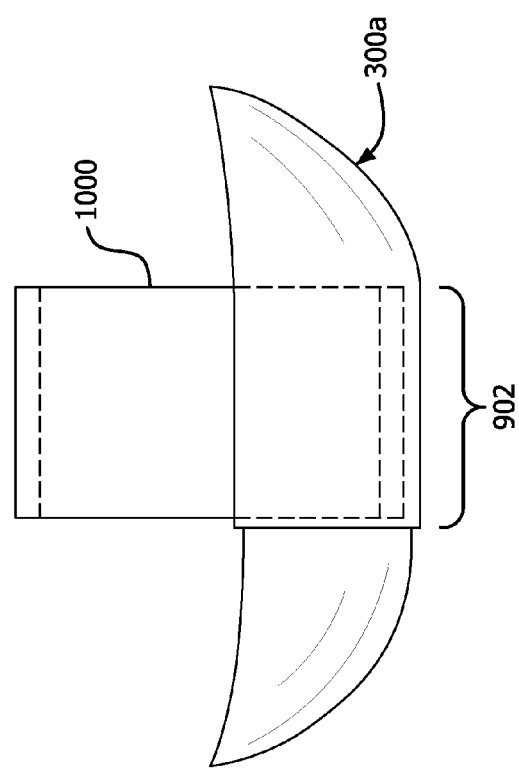

FIGS. 10A through 10C describe a method used to bond the first cover body portion 312 and second cover body portion 318 together. Shown in FIG. 10A is a ring 1000 having a length 902a that approximates the working length 902. As shown in FIGS. 10B and 10C, the ring 1000 can be inserted into the cup-shaped assembly 300a. As shown in FIG. 10C, the ring 1000 has a diameter 1010 dimensioned to mate into the cup-shaped assembly 300a. A layer of high temperature polymeric film, such as Kapton® can then be circumferentially wrapped around the ring 1000 and cup-shaped assembly 300a after the ring 1000 is inserted into the cup-shaped assembly 300a. A high temperature fiber can be circumferentially wrapped about the high temperature polymeric film, the ring 1000 and cup-shaped assembly 300a. When heated, the high temperature fiber can be operable to shrink and contract about the high temperature polymeric film and the ring 1000 and cup-shaped assembly 300a, and therefore apply pressure onto the overlapped first cover body portion 312 and second cover body portion 318. After securing the high temperature fiber the components can be heated in an air convection oven to about 250° C. for about 30 minutes. The pressure applied by the contracting high temperature fiber causes the thermoplastic layers within the overlapped first cover body portion 312 and second cover body portion 318 to reflow and form a bond between the layers.

The assembly can then be ambient forced air cooled for about 30 minutes. The high temperature fiber, high temperature film and the ring 1000 can be removed and the bonded first and second cover portions can be expanded to form the balloon cover 300. A compacted balloon mounted onto a catheter can be inserted into the balloon cover 300 thereby forming a covered balloon as previously described in FIG. 3A. The balloon can be inflated to conform to the balloon cover and then can be partially deflated. While the balloon is partially deflated, an adhesive can be injected into the balloon cover apertures (316, 322 of FIG. 9A) to bond the opposing ends of the balloon cover to the underlying balloon. The adhesive can be cured forming a catheter system having a balloon 200 and a balloon cover 300 in accordance with an embodiment, as depicted in FIGS. 1A and 1B. In an embodiment, the balloon cover 300 does not cover the balloon leg portions 204 (see FIG. 2) of the balloon 200. In another embodiment, the balloon cover 300 is not attached to a catheter, or any other structure that a balloon 200 is mounted.

The balloon cover in accordance with embodiments herein are scalable to different size balloons. Thus, a 24 mm to 37 mm diameter balloon with the cover in accordance with an embodiment may have a burst pressure of 9 atmospheres (atm) to 20 atm. Similarly smaller diameter balloons, e.g. a 5 mm diameter balloon can be converted to a high pressure balloon by the addition of a balloon cover in accordance with embodiments provided herein. In an embodiment, a 29 mm balloon with a rated burst pressure of 3 atm may be converted to a high pressure balloon with a burst pressure of about 11 atm with the addition of a balloon cover in accordance with embodiments provided herein. In another embodiment, a 5 mm diameter balloon may have a burst pressure of about 45 atm with the addition of a balloon cover in accordance with embodiments provided herein.

An embodiment of a balloon catheter system comprises a balloon catheter comprising an inflatable medical balloon having a balloon working length and an expanded and unexpanded diameter, and a balloon cover having a length and an expanded and unexpanded diameter, wherein the balloon cover comprises a first cover portion and a second cover portion, wherein the first cover portion and second cover portion each comprise a cover body portion integrally connected to a cover taper portion having an aperture located at an apex of the cover taper portion, and wherein the cover taper portions of the first cover portion and second cover portion are located at opposite ends of the balloon cover and the first cover body portion and second cover body portion overlap for a substantial portion of the balloon working length defining a cover working length. In another embodiment, the medical balloon is a non-compliant balloon. In another embodiment, the medical balloon is a compliant balloon. In another embodiment, the balloon cover comprises a fibrillated material. In another embodiment, the fibrillated material is ePTFE. In another embodiment, fibrils in the ePTFE are oriented in a radial direction.

In another embodiment, the balloon cover comprises strips of ePTFE that are adhered to each other. In another embodiment, the strips are laid in multiple angular orientations on the cover body portions and the cover taper portions of the balloon cover. In another embodiment, the balloon cover is adhered to the medical balloon. In another embodiment, the cover working length overlaps a portion of a balloon taper portion. In another embodiment, the expanded diameter of the balloon cover is smaller than the expanded diameter of the medical balloon.

In accordance with another embodiment, a balloon cover comprises a length, an unexpanded and expanded diameter, and first and second cover portions, wherein the first and second cover portions each comprise a cover body portion integrally connected to a cover taper portion having an aperture located at an apex of the cover taper portion, and wherein the cover taper portion of the first cover portion and second cover portion are located at opposite ends of the balloon cover and the first and second cover body portions overlap for a substantial portion of the length of the balloon cover.

Various alternative embodiments can be fabricated. For example, embodiments of balloon covers can incorporate additional balloon cover portions so that a balloon cover has more than two cover portions. A balloon cover in accordance with embodiments can have two, three, four, five, six, seven, eight, nine, ten or more sequentially overlapping portions. Balloon covers can also be formed to have cover taper portions of various lengths and/or non-circular cross-sectional profiles. Embodiments of balloon covers can also incorporate strengthening elements such as high strength fibers, braids or other elements to enhance the balloon cover strength or rigidity. Balloon covers in accordance with embodiments can also incorporate surface treatments to provide drugs, therapeutic agents, lubricious coatings or radiopaque markings. A guidewire channel can also be provided between a balloon and a balloon cover resulting in an optional "rapid exchange" configuration.

Figure 12A:
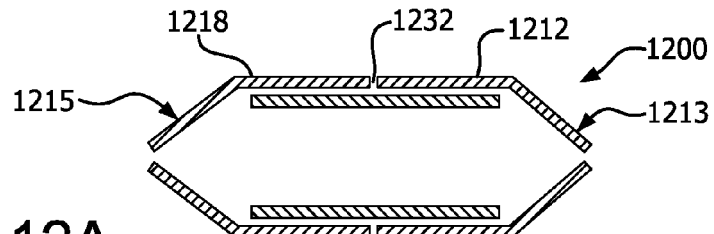
FIG. 12A is a cross-sectional side view of a balloon cover incorporating an intermediate cover portion, in accordance with an embodiment.

In accordance with other embodiments, FIGS. 12A through 12E show side cross-sectional views of embodiments of balloon covers comprising a first cover portion 1213 and a second cover portion 1215 along with various intermediate cover portions. FIG. 12A is a side cross-sectional view of a balloon cover 1200 comprising a first cover portion 1213, a second cover portion 1215, and an intermediate cover portion 1230. The first cover portion 1213 and the second cover portion 1215 are co-axially aligned and closely abutted defining a gap 1232. The intermediate cover portion 1230 bridges the gap 1232 and is overlapped at least partially by a first cover body portion 1212 and a second cover body portion 1218.

Figure 12B:
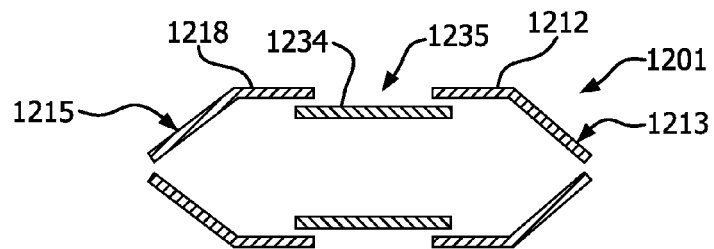
FIG. 12B is a cross-sectional side view of a balloon cover incorporating an intermediate cover portion, in accordance with another embodiment.

FIG. 12B is a side cross-sectional view of a balloon cover 1201 comprising a first cover portion 1213, a second cover portion 1215, and an intermediate cover portion 1234. The first cover portion 1213 and the second cover portion 1215 are co-axially aligned and spaced apart defining a gap 1235. The intermediate cover portion 1234 bridges the gap 1235 and is overlapped at least partially by a first cover body portion 1212 and a second cover body portion 1218.

Figure 12C:
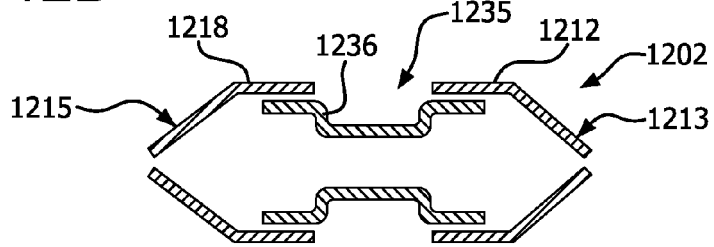
FIG. 12C is a cross-sectional side view of a balloon cover incorporating an intermediate cover portion, in accordance with another embodiment.

FIG. 12C is a side cross-sectional view of a balloon cover 1202 comprising a first cover portion 1213, a second cover portion 1215, and an intermediate cover portion 1236. The intermediate cover portion 1236 defines a stepped diameter that is smaller than diameters of the first and second balloon cover portions. The first cover portion 1213 and the second cover portion 1215 are co-axially aligned and spaced apart defining a gap 1235. The intermediate cover portion 1236 bridges the gap 1235 and is overlapped at least partially by a first cover body portion 1212 and a second cover body portion 1218.

Figure 12D:
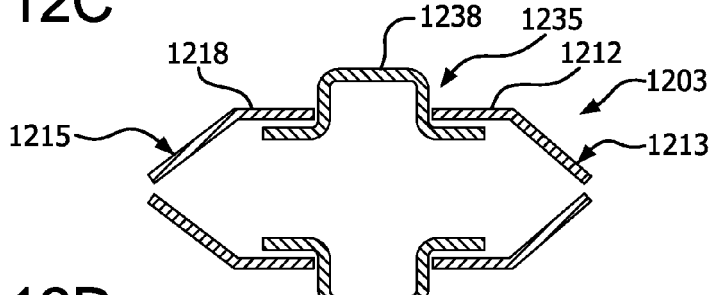
FIG. 12D is a cross-sectional side view of a balloon cover incorporating an intermediate cover portion, in accordance with another embodiment.

FIG. 12D is a side cross-sectional view of a balloon cover 1203 comprising a first cover portion 1213, a second cover portion 1215, and an intermediate cover portion 1238. The intermediate cover portion 1238 defines a stepped diameter that is larger than diameters of the first and second balloon cover portions. The first cover portion 1213 and the second cover portion 1215 are co-axially aligned and spaced apart defining a gap 1235. The intermediate cover portion 1238 bridges the gap 1235 and is overlapped at least partially by a first cover body portion 1212 and a second cover body portion 1218.

Figure 12E:
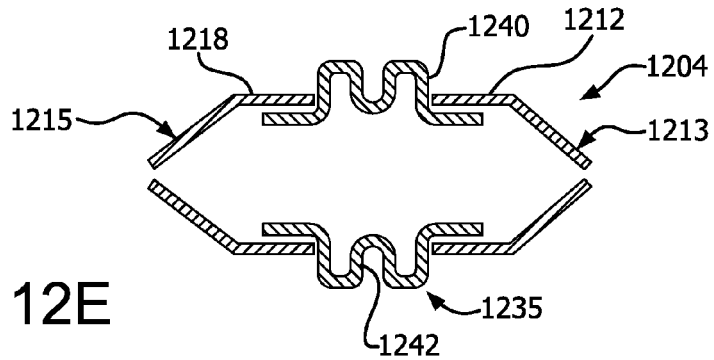
FIG. 12E is a cross-sectional side view of a balloon cover incorporating an intermediate cover portion, in accordance with another embodiment.

FIG. 12E is a side cross-sectional view of a balloon cover 1204 comprising a first cover portion 1213, a second cover portion 1215, and an intermediate cover portion 1240. The intermediate cover portion 1240 defines a stepped diameter that is larger than diameters of the first and second balloon cover portions. The intermediate cover portion 1240 incorporates a groove 1242 along a circumference of the intermediate cover portion 1240. The first cover portion 1213 and the second cover portion 1215 are co-axially aligned and spaced apart defining a gap 1235. The intermediate cover portion 1238 bridges the gap 1235 and is overlapped at least partially by a first cover body portion 1212 and a second cover body portion 1218.

Balloon covers of embodiments provided herein may incorporate one, two, three, four, five or more additional intermediate cover portions. The intermediate cover portions can have similar or dissimilar shapes or profiles and can be configured for a specific application. For example, a stepped intermediate cover portion can be configured to expand and anchor a heart valve stent. In another embodiment the stepped intermediate cover portion can be configured to expand and anchor a vein valve, a pulmonary valve or a non-cylindrical stent.

In accordance with another embodiment, a balloon cover is provided comprising a length, a first cover portion and a second cover portion, an unexpanded and expanded diameter, and an intermediate portion comprising an intermediate portion first end and an intermediate portion second end opposite the intermediate portion first end, wherein the first cover portion and second cover portion each comprise a cover body portion integrally connected to a cover taper portion having an aperture located at an apex of the cover taper portion, wherein the cover taper portions of the first cover portion and second cover portions are located at opposite ends of the balloon cover and wherein the intermediate portion first end overlaps with at least a portion of the cover body portion of the first cover portion and the intermediate portion second end overlaps with at least a portion of the cover body portion of the second cover portion.

In accordance with another embodiment, a balloon cover is provided comprising a length, a first cover portion and a second cover portion, an unexpanded and expanded diameter, and an intermediate portion comprising an intermediate portion first end and an intermediate portion second end opposite the intermediate portion first end, wherein the first cover portion and second cover portion each comprise a cover body portion integrally connected to a cover taper portion having an aperture located at an apex of the cover taper portion, wherein the cover taper portions of the first cover portion and second cover portions are located at opposite ends of the balloon cover and wherein the intermediate portion first end overlaps with at least a portion of the cover body portion of the first cover portion and the intermediate portion second end overlaps with at least a portion of the cover body portion of the second cover portion. In another embodiment, when the balloon cover is in its expanded diameter, the intermediate section confers to the balloon cover a shape selected from the group consisting of an hourglass, triangular, square, rectangular, oval or other polygon. In another embodiment, the intermediate section comprises a different material than the first cover portion and second cover portion. In another embodiment, the intermediate section comprises ePTFE.

Figure 13:
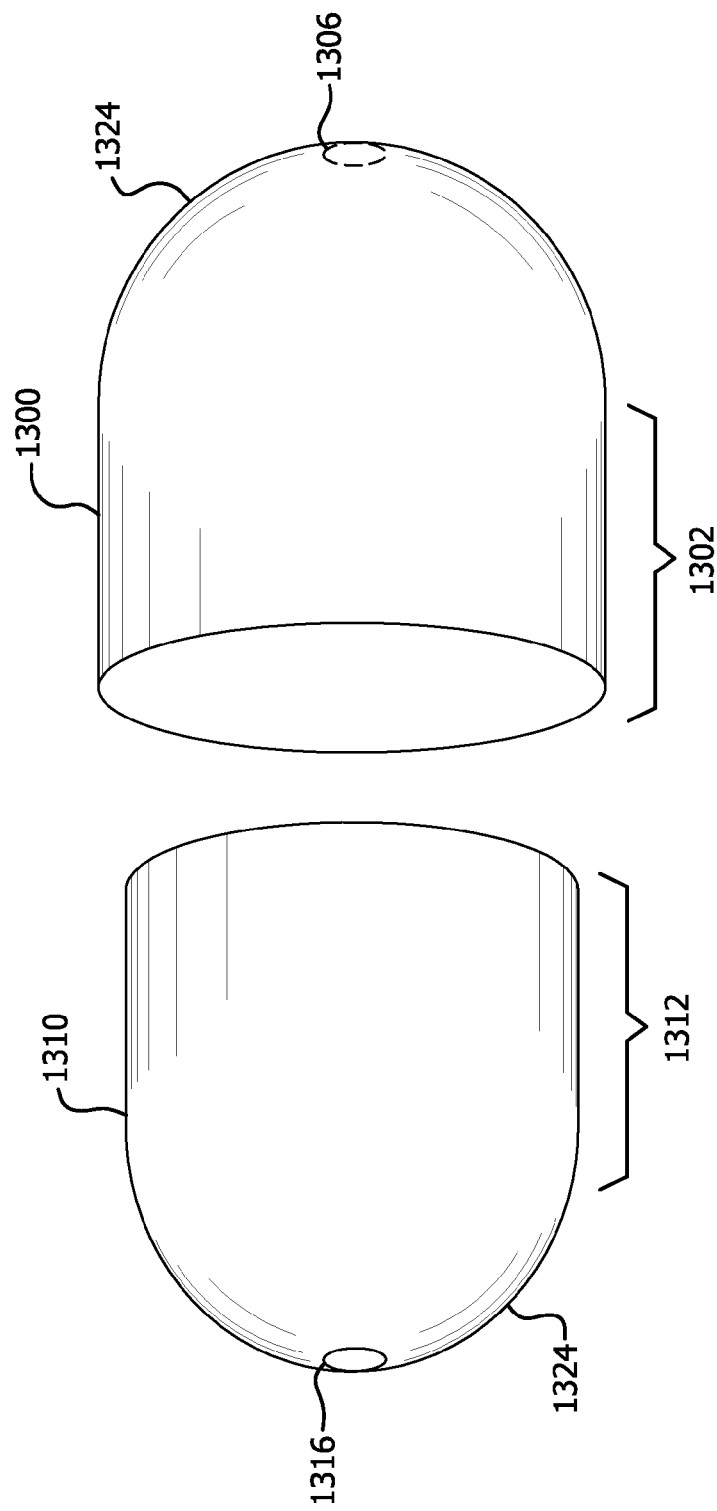
FIG. 13 is a perspective view of a first cover portion and a second cover portion having essentially spherical taper portions in accordance with an embodiment.

It is understood that the cover taper portions may define any suitable shape complementary to the shape of an inflated balloon. Referring again to FIG. 8A, the first cover taper portion 314 and the second cover taper portion 320 define a conical shape. FIG. 13 is a side perspective view of another balloon cover 1300, in accordance with an embodiment. The balloon cover 1300 is substantially similar to the embodiment as shown in FIG. 8A, but for comprising a first cover taper portion 1324 and a second cover taper portion 1324 defining a spherical shape.

In various alternate balloon configurations, the balloon and balloon covers in accordance with embodiments provided herein may incorporate additional cover layers that can alter the properties of the balloon or of the balloon system. In particular, additional balloon covers can alter the balloon shape as the balloon is inflated. Other additional covers, in accordance with embodiments, can alter or enhance the inflation profiles of a balloon. In addition, cover leg portions may be provided to the balloon cover that is complementary to the balloon leg portions 204, as shown in FIG. 3A, to allow the high-strength bonding of the balloon covers to the balloon. In one embodiment, the additional balloon covers comprise a frangible balloon cover. In another embodiment, the frangible balloon cover comprises ePTFE.

EXAMPLES

Without intending to limit the scope of the invention, the following examples illustrate how various embodiments of the invention may be made and/or used Example 1

A balloon cover in accordance with an embodiment was fabricated according to the previously described methods, with the following additional details:

A mandrel was provided that had the following dimensions: first cylindrical portion diameter was 1.142", first cylindrical portion length was 1.378", second cylindrical portion diameter was 1.130", second cylindrical portion length was 1.378", the opposing taper portions had 90° included angles and the opposing shafts had diameters of 0.157". The mandrel was fabricated from 300 series stainless steel.

The manufacturing aid (film) was about 0.75 wide and about 8" long. The film strap comprised a densified fluoropolymer as described in U.S. Pat. No. 7,521,010 to Kennedy et al., laminated with a fluoroelastomer thermoplastic adhesive, as described in U.S. Pat. No. 7,462,675 to Chang et al. The film had the following properties:
Composite thickness=5 μm
Composite mass per area=11.1 g/m2
Machine Direction Matrix Tensile Strength=356 MPa.

Three full circumferential wraps were layered onto the mandrel. The heat-tacking soldering iron was set to about 650° F.

The film straps were about 0.75" wide and were of the same film as the manufacturing aid described above. The circumferential wrapped film was about 1" wide and was of the same film as the manufacturing aid described above.

The heat treat temperature was about 250° C. and the heat treatment time was about 30 minutes.

The first and second cover portions were cut to have cover body portions of about 25 mm.

The metallic ring had a length of about 24 mm, an outer diameter of about 38 mm, an inner diameter of about 35 mm and was fabricated from 300 series stainless steel. The high temperature polymeric film was 0.004" thick, 40 mm wide Kapton®. The high temperature fiber was a heat shrinkable fluoropolymer. The heat treat temperature was about 250° C. and the heat treatment time was about 30 minutes.

The balloon was fabricated from Polyethylene Terephthalate (PET, Thermoplastic Polyester) and had a nominal outer diameter of about 29 mm, a nominal working length of about 26 mm, a nominal wall thickness (along the working length) of about 0.0028", included cone angles of about 90° and opposing leg portion outer diameters of about 3.4 mm. The balloon cover was slidingly engaged over the balloon and was bonded to the underlying balloon with LOCTITE® adhesive part number 495 and was then ambient cured.

The balloon cover was undersized, relative to the balloon inflated diameter, by about 5%, allowing the balloon cover to absorb the load imparted to the cover by the inflated balloon.

Example 2

The balloon with attached balloon covers from Example 1 was subjected to a pull through test. The pull through test was designed to measure the force required to pull a deflated balloon through a series of gage holes. The test was designed to emulate the force required to retract a deflated balloon back into an introducer sheath.

A vertical universal mechanical testing system (Instron®, Model 5564, Norwood, Mass., USA) with a 10.2 kg tension load cell was configured to measure pull through forces. A water bath was aligned to the testing system and heated to about 37° C. A longitudinally split gage, having a series of varying diameter pull through holes was fixed within the heated water bath.

A balloon catheter with an attached balloon cover from Example 1 was provided. A distal portion of the balloon catheter shaft was clamped to the load cell head. The gage with a series of varying diameter pull through holes was "split open" to allow a proximal portion of the catheter shaft to be inserted into a first, large diameter hole (22 F or about 0.29" with a chamfered/broken edge lead in). The gage halves were then aligned and clamped together, surrounding the proximal portion of the catheter shaft. The balloon was then inflated to about 2 atm and then deflated with a vacuum. The vacuum was maintained with a stopcock located on the proximal end of the catheter. The deflated balloon with balloon cover was then pulled up through the gage hole at rate of about 10"/minute while the instant pull force was recorded.

The gage was then opened and the catheter shaft was positioned into the next smaller gage hole. The gage was reassembled, the balloon was re-inflated to about 2 atm and deflated as previously described. The deflated balloon with balloon cover was then pulled through the gage hole while the instant pull force was recorded.

The test sequence was repeated using progressively smaller gage pull through holes. The test sequence was terminated if the balloon ruptured or leaked during inflation, or if the pull force exceeded a pre-determined limit. The pull through hole diameters for a typical 29 mm underlying balloon with balloon cover according to Example 1 ranged from 22 F (about 0.29") to 11 F (about 0.145").

Balloons without a balloon cover in accordance with embodiments provided herein were also evaluated on the pull through test to generate comparative data.

Example 3

A balloon with attached balloon cover from Example 1 was subjected to a balloon compliance, inflation/burst test. The balloon compliance, inflation/burst test was designed to measure the balloon diameter vs. internal pressure along with determining the internal balloon pressure required to rupture/burst the balloon with attached balloon cover from Example 1.

A balloon compliance/burst test system was provided (Interface Associates, Laguna Niguel, Calif., USA, Model PT3070). The test system had a water bath heated to about 37° C., a pressurized water feed/pressure measurement system, and a laser micrometer to measure the outer diameter of the expanded balloon and balloon cover. The balloon compliance/burst test parameters are displayed in TABLE 1 below:

TABLE 1

| Test Parameter | Setting |
| --- | --- |
| Pressurization Ramp Rate (ml/s) | 1.0 |
| Pressurization Alarm Drop | 2.50 |
| Pressurization Time* (sec) | |
| Pressurization Max Pressure (atm) | 50.00 |
| Pressurization Max Volume (ml) | 200.00 |
| Pressurization Max Diameter (mm) | 55.00 |
| Start Up Position | 0.10 |
| Start Up Vacuum Pressure | −0.50 |
| Pressure Units | atm |
| Diameter Units | mm |
| Ramp Target Offset Pressure (atm) | 0.00 |
| Pre-Fill Volume (ml) | 20.00 |
| Pre-Fill Pressure (atm) | 1.00 |
| Pre-Fill Rate (ml/s) | 0.50 |

The balloon with attached balloon cover was purged of air by a series of vacuum air withdrawals followed by water inflations. The purging was repeated until no more air could be withdrawn from the balloon catheter. After air purging, the catheter was subjected to the compliance/burst test.

Balloons without the balloon cover in accordance with embodiments provided herein were also evaluated on the compliance/burst test to generate comparative data.

Example 4

Balloons with attached cover from Example 1 were subjected to the pull through test (Example 2) and to the balloon compliance, inflation/burst test (Example 3). Additionally, balloons without a balloon cover were subjected to the pull through and compliance/burst test to generate comparative data. The test results are displayed in FIGS. 11A and 11B.

These data show that the presence of a balloon cover in accordance with embodiments provided herein significantly raises the burst strength of the balloon with balloon cover system without significantly compromising the pull through force.

Balloon covers in accordance with embodiments provided herein increases the strength of a balloon to attain a higher rated burst pressure while maintaining a low delivery profile. Further, balloon covers in accordance with embodiments provided herein control the profile of the balloon during inflation providing a consistent and uniform diameter along the working length of the balloon.

Balloon covers may prevent one end of the balloon from attaining an expanded diameter prior to the opposing end, or the middle of the balloon prior to the ends. This consistency of profile during inflation decreases the likelihood that a stent will be dislodged longitudinally along the length of the balloon moving either partially or fully off the balloon. The consistency of profile during inflation decreases the likelihood for vessel trauma as a stent is evenly expanded and subsequently evenly engages a vessel wall.

In accordance with another embodiment, a balloon cover is provided that is operable to provide one or more intermediate inflated diameters that are apparent to a doctor during delivery that provides a uniform profile (that is, a relatively uniform diameter) along the length of the balloon at each intermediate diameter. In accordance with an embodiment, a balloon cover is provided that is operable such that the balloon may inflate to an intermediate diameter at a first pressure and a second diameter larger than the intermediate diameter at a second pressure.

In accordance with another embodiment, a balloon cover is provided that is operable to provide one or more intermediate inflated diameters that are apparent to a doctor during delivery that provides a uniform profile (that is, a relatively uniform diameter) along the length of the balloon at each intermediate diameter, wherein the balloon is non-compliant. Non-compliant as defined herein is a characteristic of a balloon that, by itself, inflates to a preset diameter even as pressure is increased. Compared with a balloon comprising a material that may stretch under increasing pressure which is therefore considered to be compliant. In accordance with an embodiment, a balloon cover is provided that is operable such that the balloon may inflate to an intermediate diameter at a first pressure and a second diameter larger than the intermediate diameter at a second pressure.

Figure 15A:
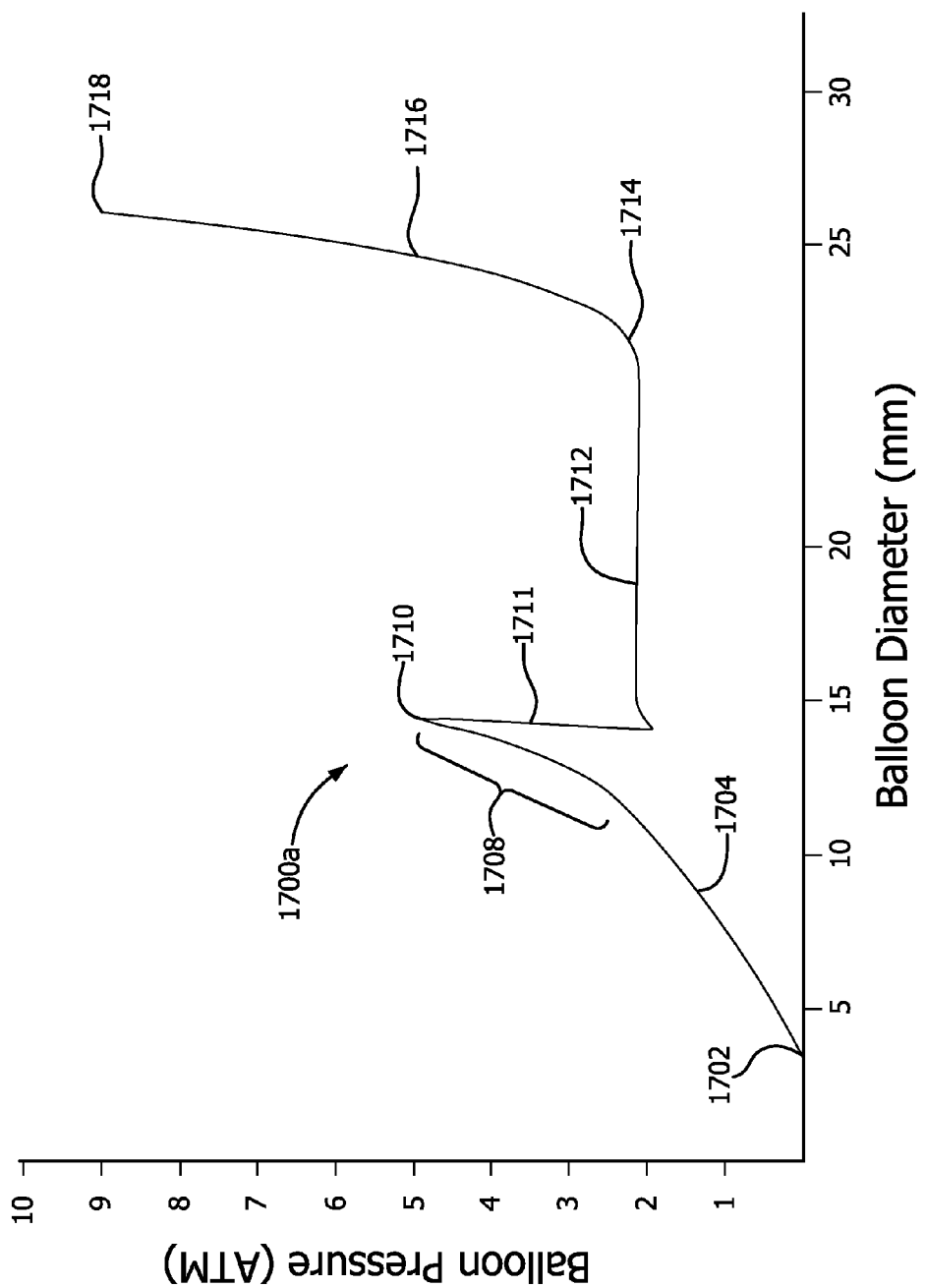
FIG. 15A is a balloon diameter vs. pressure profile generally depicting an inflation sequence of the balloon described in FIG. 16, in accordance with an embodiment.

FIG. 15A is a balloon diameter vs. balloon pressure graph, generally depicting an inflation sequence 1700*a* of a balloon cover system comprising means operable to provide an intermediate and final inflated diameter that is apparent to a doctor during delivery that provides a uniform profile (that is, a relatively uniform diameter) along the length of the balloon at each intermediate and final diameters. The balloon has an initial diameter in an un-inflated state of about 4 mm (1702). As pressure increases in the balloon, the balloon diameter increases (1704) to an intermediate diameter of about 14 mm while the pressure increases to about 5 atm (1708). At about 5 atm with the balloon at an approximate 14 mm diameter, the means operable to provide an intermediate and final inflated diameter allows the balloon to continue to expand (1710) while at an approximate pressure of 2 atm (1712). At a diameter of about 23 mm, the balloon and balloon cover resist further expansion and the pressure begins to rise (1714). As the pressure increases above 2 atm the balloon remains at essentially 25 mm (1716) which may be the final diameter that is desired for the particular purpose.

The relatively more rapid increase in pressure between about 2 atm and 5 atm at (1708) may provide for the balloon to establish a uniform profile (diameter) along the length of the balloon. For example, but not limited thereto, any folds, wrinkles or other uneven inflation profile of the balloon along the length of the balloon caused by being compressed onto the catheter shaft have been smoothed out under the inflation pressure at (1708). The increase in pressure at (1708) provides the doctor tactile feedback that the balloon has expanded to about the intermediate diameter. The rapid drop in pressure at (1711) provides the doctor tactile feedback that the balloon has been released to allow further expansion. The increase in diameter at a relatively uniform pressure at (1712) provides that the balloon may expand while retaining a uniform profile (diameter) along the length of the balloon. The increase in pressure at (1714) provides the doctor tactile feedback that the balloon has expanded to about the final diameter.

Figure 15B:
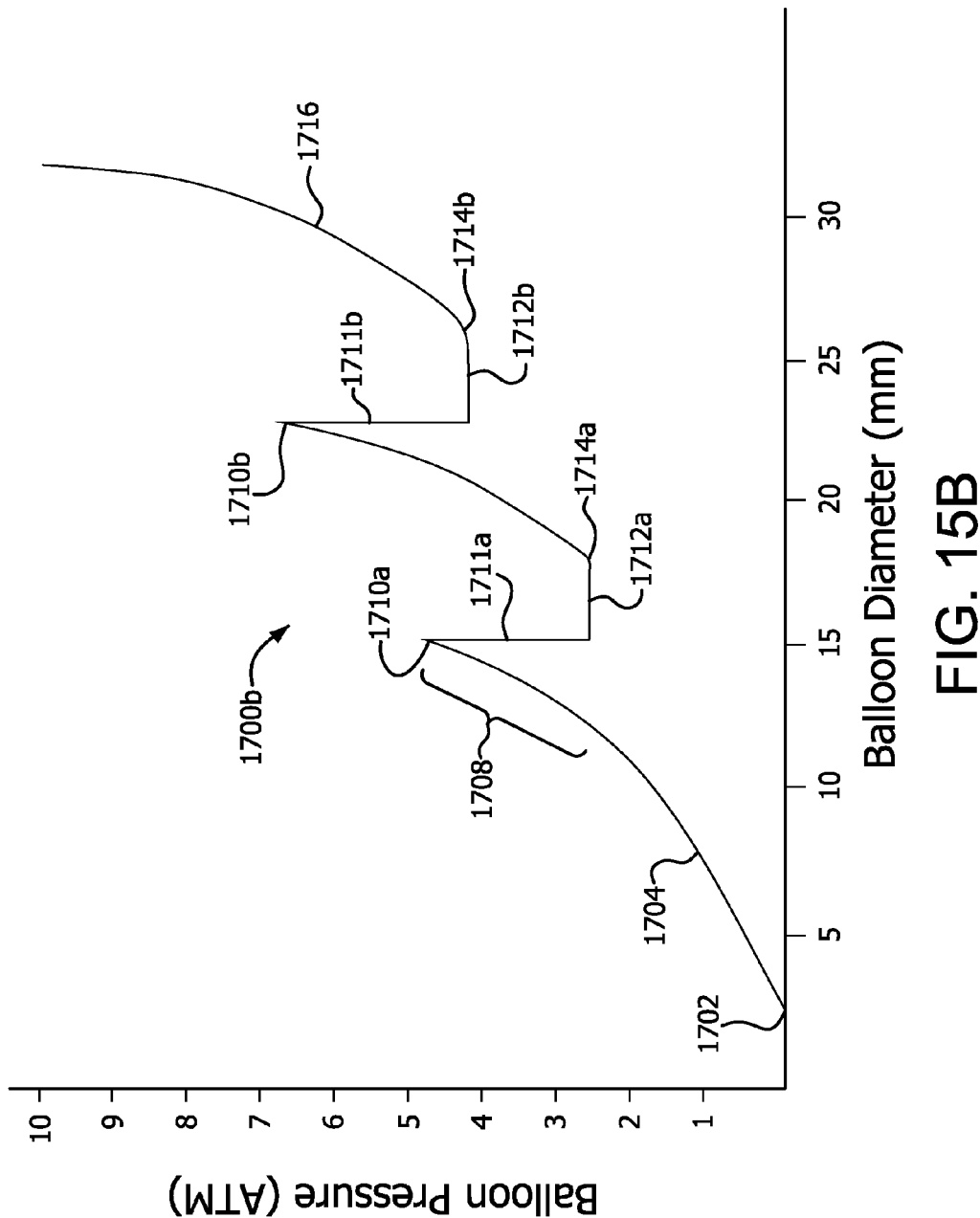
FIG. 15B is a balloon diameter vs. pressure profile generally depicting an inflation sequence of the balloon, in accordance with an embodiment.

FIG. 15B is a balloon diameter vs. balloon pressure graph generally depicting an inflation sequence 1700b of a balloon cover system comprising means operable to provide multiple intermediate diameters and a final inflated diameter that is apparent to a doctor during delivery that provides a uniform profile (that is, a relatively uniform diameter) along the length of the balloon at each intermediate and final diameters. The balloon has an initial diameter in an uninflated state of about 4 mm (1702). As pressure increases in the balloon, the balloon diameter increases (1704) to a first intermediate diameter of about 14 mm (1710a) while the pressure increases to about 5 atm. At about 5 atm with the balloon at an approximate 14 mm diameter, the means operable to provide multiple intermediate and final inflated diameters allows the balloon to continue to expand (1710a) while at an approximate pressure of 2 atm (1712a). As the pressure increases to above 2 atm (1714a), the balloon remains at approximately 23 mm (1710b). At about 7 atm with the balloon at an approximate 23 mm diameter, the means operable to provide multiple intermediate and final inflated diameters allows the balloon to continue to expand (1710b) while at an approximate pressure of 4 atm. At a second intermediate diameter of about 26 mm, the balloon and balloon cover resist further expansion (1714b). As the pressure increases to above 4 atm, the balloon remains at approximately 26 mm (1716) which may be the final diameter that is desired for the particular purpose.

The relatively more rapid increase in pressure between about 2 atm and 5 atm at (1708) may provide for the balloon to establish a uniform profile (diameter) along the length of the balloon. For example, but not limited thereto, any folds, wrinkles or other uneven inflation profile of the balloon along the length of the balloon caused by being compressed onto the catheter shaft have been smoothed out under the inflation pressure at (1708). The increase in pressure at (1708) provides the doctor tactile feedback that the balloon has expanded to about the first intermediate diameter. The rapid drop in pressure at (1711a) provides the doctor tactile feedback that the balloon has been released to allow further expansion. The increase in diameter at a relatively uniform pressure at (1712) provides that the balloon may expand while retaining a uniform profile (diameter) along the length of the balloon. The increase in pressure at (1714a) provides the doctor tactile feedback that the balloon has expanded to about the second intermediate diameter. The rapid drop in pressure at (1711b) provides the doctor tactile feedback that the balloon has been released to allow further expansion. The increase in pressure at (1714b) provides the doctor tactile feedback that the balloon has expanded to about the final diameter.

The compliance (pressure vs. diameter) curve as provided in accordance with the embodiments of FIGS. 15A and 15B with various points along the curve is operable to deliver a stent that is on the balloon in a uniform profile along the length of the stent in a predictable manner at an intermediate diameter. Further, an inflation profile as provided in accordance with the embodiments of FIGS. 15A and 15B is operable to deliver a stent that is on the balloon with a uniform profile along the length of the stent with increasing diameter that provides the doctor with a safe, customizable intermediate diameter for which to deliver the stent.

In accordance with an embodiment, means operable to provide an intermediate and final inflated diameter to a balloon that is apparent to a doctor during delivery that provides a uniform profile (that is, a relatively uniform diameter) along the length of the balloon at each intermediate and final diameters comprises a frangible balloon cover operable to allow the balloon to inflate to a predetermined diameter while allowing the balloon to have a substantially uniform diameter along the working length of the balloon. Then, as pressure increases within the balloon that is inflated from a single inflation lumen, the frangible balloon cover ruptures allowing the balloon to increase to a predetermined diameter. In an embodiment, the balloon increases in diameter evenly along the working length of the balloon.

In an embodiment, an external constraint allows the balloon to open to a predetermined intermediate diameter that is less than the fully expanded working diameter of the balloon. An external constraint is any element that resides outside of the balloon. The external constraint allows the balloon to have a substantially uniform diameter long the working length of the balloon. As pressure increases within the balloon that is inflated from a single inflation lumen, the external constraint releases the balloon at a predetermined pressure allowing the balloon to increase in diameter. In an embodiment, the balloon increases in diameter substantially uniformly along the working length of the balloon. In accordance with embodiments, the external constraint is a frangible cover.

In accordance with an embodiment, the external constraint allows the balloon to open to a predetermined intermediate diameter that is greater than about 20% than the fully expanded working diameter of the balloon. In accordance with another embodiment, the external constraint allows the balloon to open to a predetermined intermediate diameter that is greater than about 30% than the fully expanded working diameter of the balloon. In accordance with another embodiment, the external constraint allows the balloon to open to a predetermined intermediate diameter that is greater than about 50% than the fully expanded working diameter of the balloon.

In an embodiment, a frangible balloon cover allows the balloon to open to a predetermined diameter that is less than the fully expanded working diameter of the balloon. The various covers incorporated onto balloons in accordance with embodiments provided herein allow the balloon to have a substantially uniform diameter long the working length of the balloon. As pressure increases within the balloon that is inflated from a single inflation lumen, the frangible cover breaks, allowing the balloon to increase in diameter. In an embodiment, the balloon increases in diameter substantially uniformly along the working length of the balloon.

In another embodiment, a frangible balloon cover allows the balloon to open to a predetermined diameter that is less than the fully expanded working diameter of the balloon as well as elongate to a longer working length. FIG. 17D is a side cross-sectional view of a frangible balloon assembly 1600b showing the catheter shaft 104, the balloon 200, the frangible cover 1650 and the outer cover 1616 in a state of intermediate inflation wherein the frangible cover 1650 is not ruptured and the diameter of the frangible balloon assembly 1600b is at an intermediate diameter Di and the length of the balloon L1 is smaller than the balloon working length Lw, in accordance with an embodiment. FIG. 17E is a side cross-sectional view of a frangible balloon assembly 1600b showing the catheter shaft 104, the balloon 200, the frangible cover 1650 and the outer cover 1616 in a state of inflation to the balloon working diameter wherein the frangible cover 1650 has ruptured releasing the balloon 200 to attain a final diameter Df and to the working length Lw, in accordance with an embodiment. The various covers incorporated onto balloons in accordance with embodiments provided herein allow the balloon to have a substantially uniform diameter along the working length of the balloon. As pressure increases within the balloon that is inflated from a single inflation lumen, the frangible cover breaks, allowing the balloon to increase in diameter and length. In an embodiment, the balloon increases in diameter substantially uniformly along the working length of the balloon.

In another embodiment, a stent may be placed adjacent to the frangible cover, the stent may be put directly on the frangible cover or there can be another layer on top of the frangible cover. Thus, as the balloon increases in diameter, a stent also increases in diameter to a predetermined diameter controlled by the frangible cover. At this stage the stent may have substantially the same diameter along the length of the stent. After the frangible cover breaks, the balloon and stent increase in diameter evenly along the working length of the balloon and along the length of the stent.

Figure 16A:
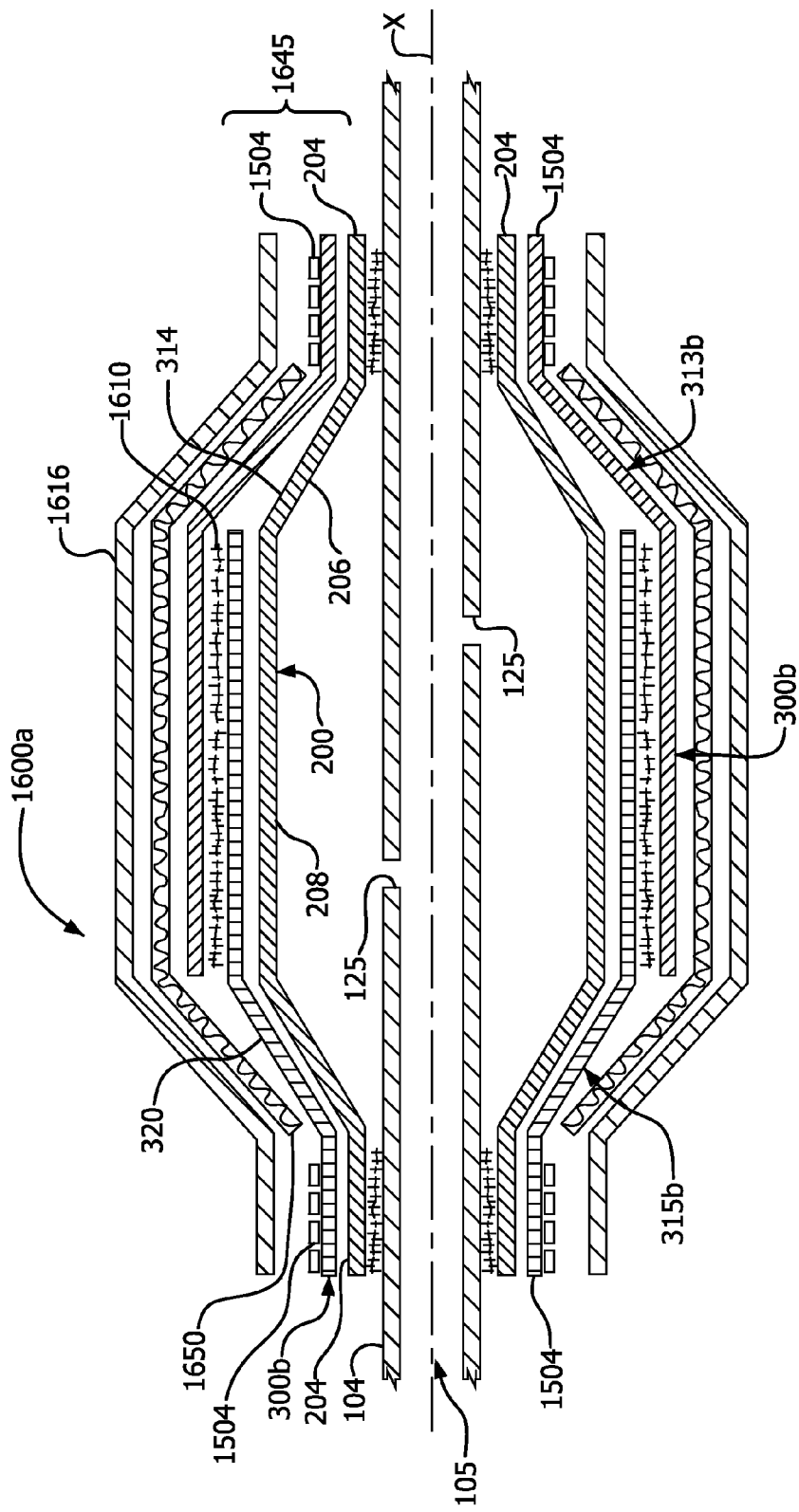
FIG. 16A is a side cross-sectional view of a frangible balloon assembly including a catheter shaft, a balloon, and a frangible balloon cover comprising a legged balloon cover and a frangible cover, in accordance with an embodiment.

FIG. 16A is a side cross-sectional view of a frangible balloon assembly 1600a including a catheter shaft 104, a balloon 200, and a frangible balloon cover 1645 comprising a legged balloon cover 300b and a frangible cover 1650, in accordance with an embodiment. Shown are the catheter shaft 104, an inflation lumen 105, and inflation ports 125 with the attached balloon 200. The balloon may be inflated from the single inflation lumen. The balloon 200 comprises balloon leg portions 204 (as also shown in FIG. 2). The balloon 200 is shown in FIG. 16A being inflated to an intermediate diameter prior to the rupturing of the frangible cover 1650. The intermediate diameter is smaller than a working diameter of the balloon 200. A working diameter of the balloon is defined as the maximum diameter of the inflated balloon. The frangible balloon cover 1645 is positioned around balloon taper portions 206 and a balloon body portion 208 of the balloon 200.

Referring again to FIGS. 8B and 16A, the legged balloon cover 300b comprises a first legged cover portion 313b and a second legged cover portion 315b. The first legged cover portion 313b includes a first cover body portion 312 integrally connected to a first cover taper portion 314, further comprising a cover leg portion 1504 located at an apex of the first cover taper portion 314. The second legged cover portion 315b includes a second cover body portion 318 integrally connected to a second cover taper portion 320, further comprising a cover leg portion 1504 located at an apex of the second cover taper portion 320.

The first cover body portion 312 is operable to overlay a portion of the balloon body portion 208. The first cover taper portion 314 is operable to overlay a portion of the balloon taper portion 206. The cover leg portion 1504 is operable to allow the balloon leg portion 204 of the balloon 200 to pass through.

The second cover body portion 318 is operable to overlay a portion of the balloon body portion 208. The second cover taper portion 320 is operable to overlay a portion of the balloon taper portion 206. The cover leg portion 1504 is operable to allow the balloon leg portion 204 of the balloon 200 to pass through.

Referring again to FIG. 16A, the first cover taper portion 314 and the second cover taper portion 320 are located at opposite ends of the balloon cover 300b. The first cover portion 313 and the second cover portion 315 are coaxially aligned along axis X and overlay the balloon 200 such that at least a portion of the first cover body portion 312 overlays at least a portion of the second cover body portion 318.

Figure 17A:
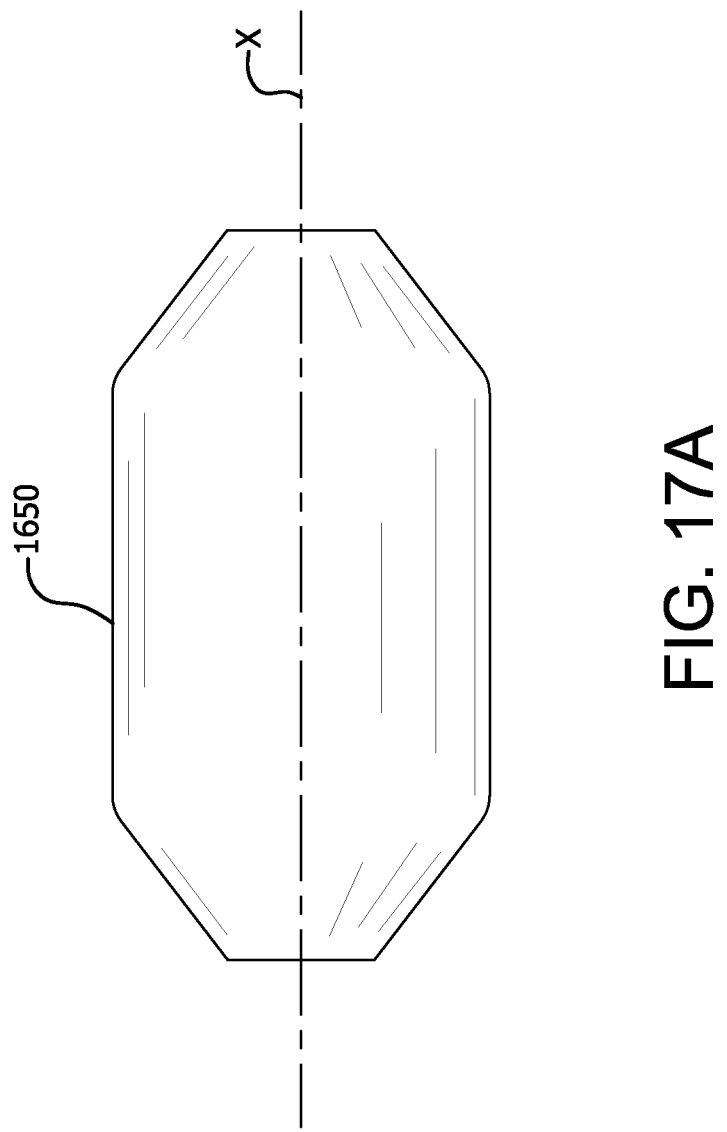
FIG. 17A is a side view of the frangible cover in accordance with an embodiment.
Figure 17D:
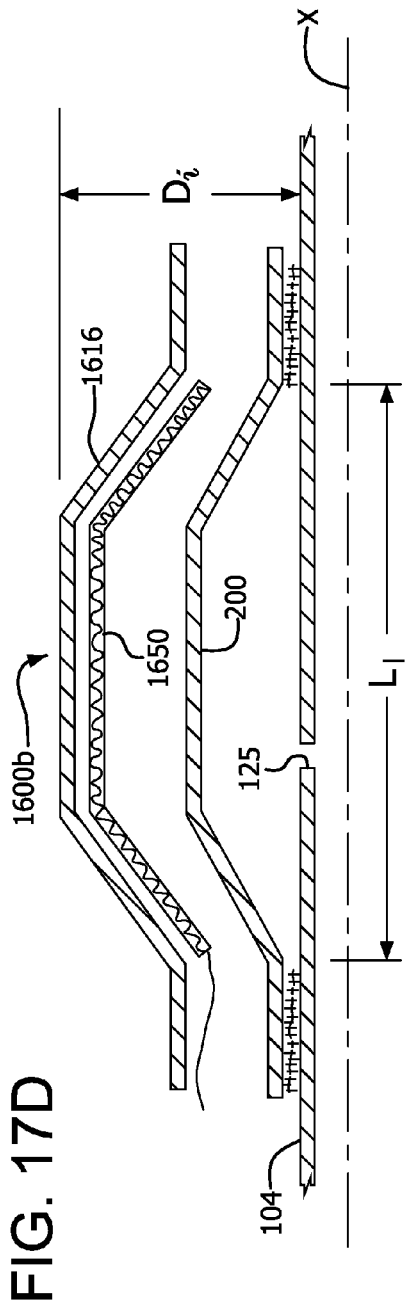
FIG. 17D is a side cross-sectional view of a frangible balloon assembly in a state of intermediate inflation wherein the frangible cover is not ruptured and the diameter and length of the frangible balloon assembly is at an intermediate diameter and length, in accordance with an embodiment.
Figure 17E:
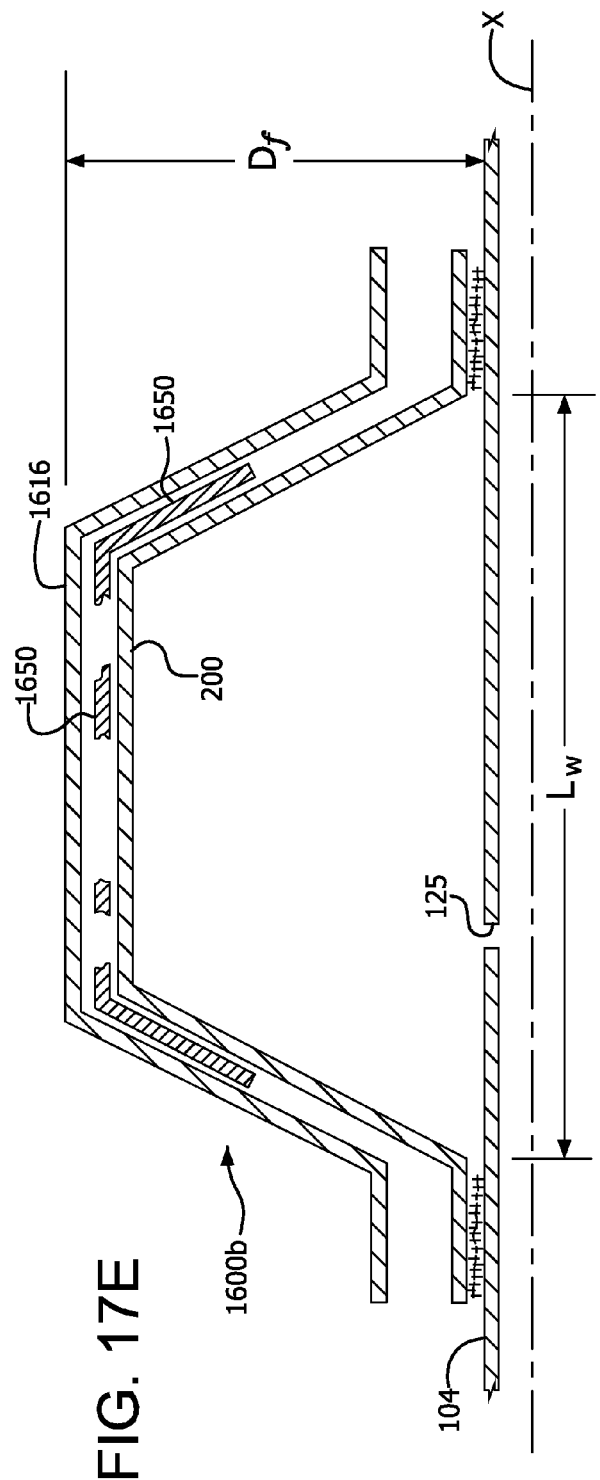
FIG. 17E is a side cross-sectional view of a frangible balloon assembly in a state of inflation to the balloon working diameter wherein the frangible cover has ruptured releasing the balloon to attain a final diameter and length, in accordance with an embodiment.

FIG. 17A is a side view of the frangible cover 1650 in accordance with an embodiment. As shown in FIG. 16A, the frangible cover 1650 overlays the first cover body portion 312, the second cover body portion 318, and at least a portion of each of the first cover taper portion 314 and the second cover taper portion 320. The frangible cover 1650 is operable to control the inflation of the balloon 200 to a first intermediate diameter that is larger than the pre-inflated diameter of the balloon 200. When the internal pressure of the balloon 200 reaches a first predetermined pressure the frangible cover 1650 is operable to rupture permitting the balloon 200 to inflate to the working diameter of the balloon 200 which is larger than the first intermediate diameter (see FIGS. 17B and 17C).

Rupturing as defined herein is to brake, tear, distort or yield, and, as used with regard to the frangible cover, rupturing of the frangible cover is operable to release the balloon from a constrained diameter allowing the underlying balloon to expand to a larger diameter.

In accordance with an embodiment, the balloon cover assembly 1600a further comprises an optional outer cover 1616 that covers the frangible cover 1650 and first cover leg portion 1504 and second cover leg portion 1504. The outer cover 1616 has a form substantially similar to the balloon as shown in FIG. 2. The outer cover 1616 may be coupled to the first cover leg portion 1504 and second cover leg portion 1504. The outer cover 1616 is operable to contain any fragments or loose edges of the frangible cover 1650 that may form as a result of the frangible cover rupturing. The optional outer cover 1616 may also be operable to prevent a stent placed thereon from sliding along the length of the balloon cover.

Figure 16B:
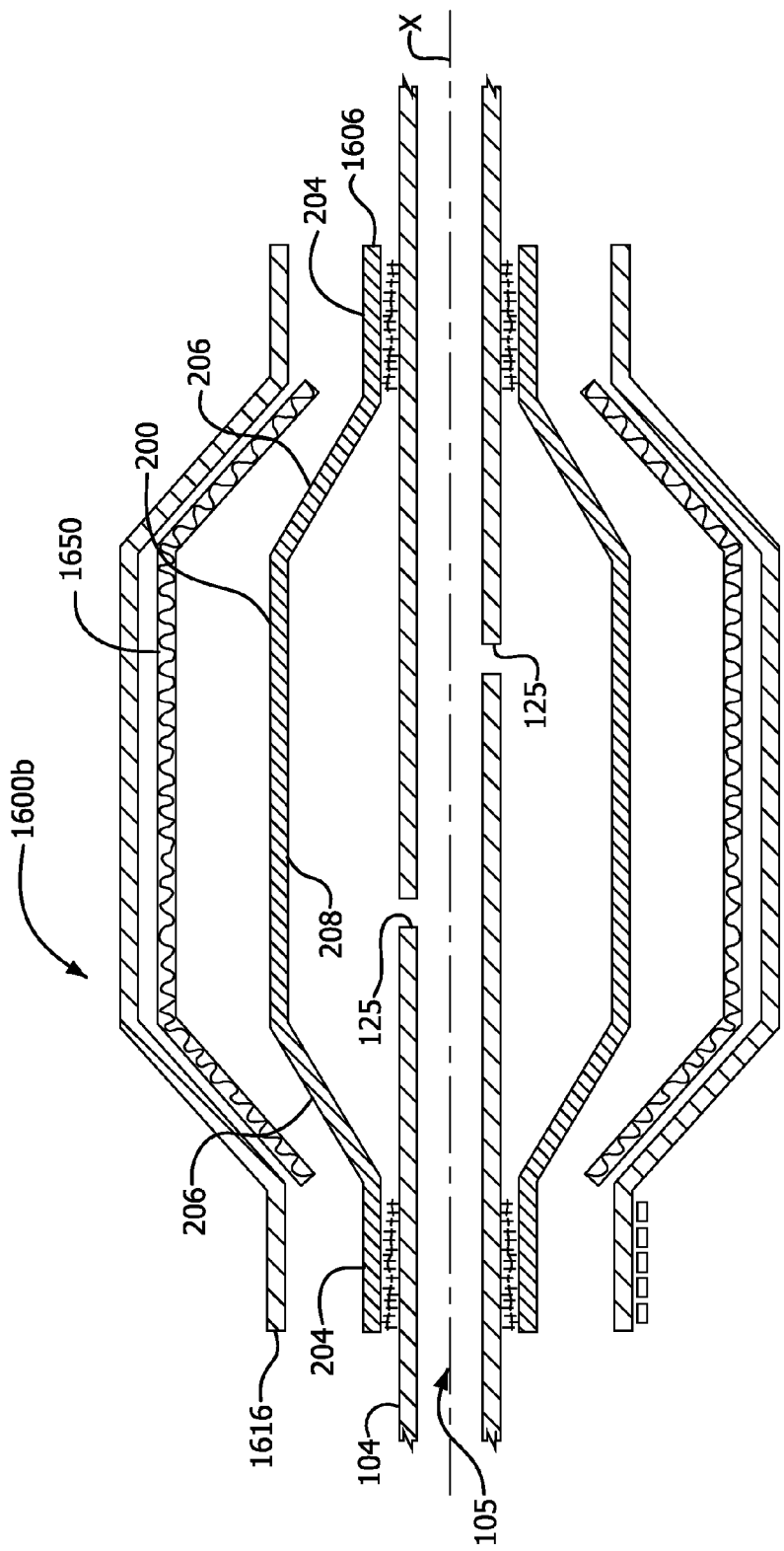
FIG. 16B is a side cross-sectional view of a frangible balloon assembly including a catheter shaft, a balloon, and a frangible cover, in accordance with an embodiment.

FIG. 16B is a side cross-sectional view of a frangible balloon assembly 1600b including a catheter shaft 104, a balloon 200, and a frangible cover 1650, in accordance with an embodiment. Shown are the catheter shaft 104, an inflation lumen 105 and inflation ports 125 with the attached balloon 200. The balloon may be inflated from the single inflation lumen. The balloon 200 comprises balloon leg portions 204 (as also shown in FIG. 2). The balloon 200 is shown in FIG. 16B being inflated to an intermediate diameter prior to the rupturing of the frangible cover 1650. The intermediate diameter is smaller than a working diameter of the balloon 200. A working diameter of the balloon is defined as the maximum diameter of the inflated balloon. The frangible balloon cover 1645 is positioned around balloon taper portions 206 and a balloon body portion 208 of the balloon 200.

FIG. 17A is a side view of the frangible cover 1650 in accordance with an embodiment. As shown in FIG. 16B, the frangible cover 1650 overlays the balloon body portion 208 and at least a portion of each of the balloon taper portions 206. The frangible cover 1650 is operable to control the inflation of the balloon 200 to a first intermediate diameter that is larger than the pre-inflated diameter of the balloon 200. When the internal pressure of the balloon 200 reaches a first predetermined pressure the frangible cover 1650 is operable to rupture permitting the balloon 200 to inflate to the working diameter of the balloon 200 which is larger than the first intermediate diameter.

FIG. 17B is a side cross-sectional view of a frangible balloon assembly 1600b showing the catheter shaft 104, the balloon 200, the frangible cover 1650 and the outer cover 1616 in a state of intermediate inflation wherein the frangible cover 1650 is not ruptured and the diameter of the frangible balloon assembly 1600b is at an intermediate diameter Di, in accordance with an embodiment. FIG. 17C is a side cross-sectional view of a frangible balloon assembly 1600b showing the catheter shaft 104, the balloon 200, the frangible cover 1650 and the outer cover 1616 in a state of inflation to the balloon working diameter wherein the frangible cover 1650 has ruptured releasing the balloon 200 to attain a final diameter Df, in accordance with an embodiment.

Rupturing as defined herein is to brake, tear, distort or yield, and, as used with regard to the frangible cover, rupturing of the frangible cover is operable to release the balloon from a constrained diameter allowing the underlying balloon to expand to a larger diameter.

In accordance with an embodiment, the balloon cover assembly 1600b further comprises an optional outer cover 1616 that covers the frangible cover 1650 and first balloon leg portion 204 and second balloon leg portion 204. The outer cover 1616 has a form substantially similar to the balloon as shown in FIG. 2. The outer cover 1616 may be coupled to the first balloon leg portion 204 and second balloon leg portion 204. The outer cover 1616 is operable to contain any fragments or loose edges of the frangible cover 1650 that may form as a result of the frangible cover rupturing. The optional outer cover 1616 may also be operable to prevent a stent placed thereon from sliding along the length of the balloon cover.

Figure 16C:
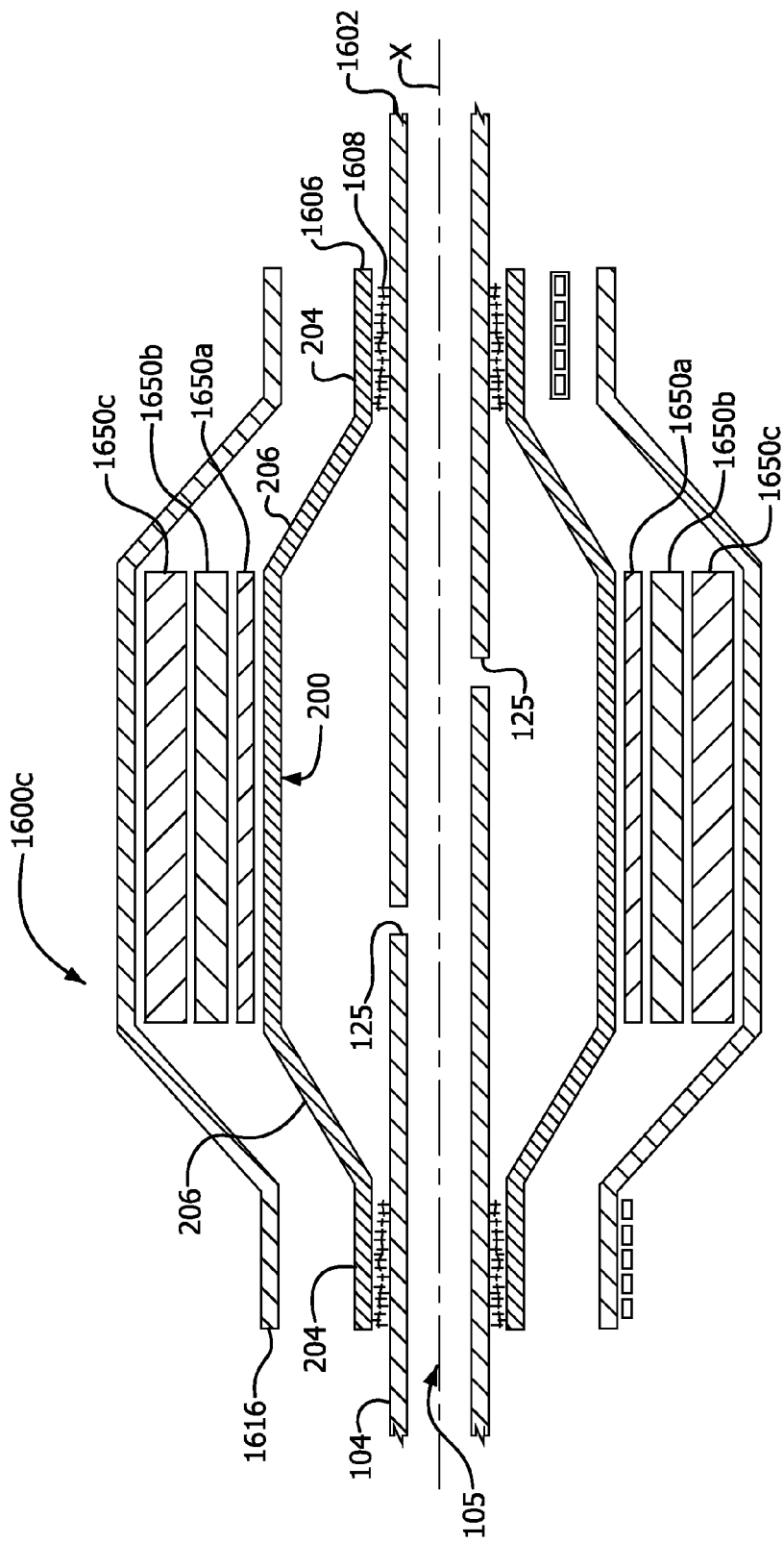
FIG. 16C is a side cross-sectional view of a frangible balloon assembly including a catheter shaft, a balloon, and a first frangible cover, a second frangible cover, and a third frangible cover, in accordance with an embodiment

FIG. 16C is a side cross-sectional view of a frangible balloon assembly 1600c including a catheter shaft 104, a balloon 200, and a first frangible cover 1650a, a second frangible cover 1650b, and a third frangible cover 1650c, in accordance with an embodiment. Shown are the catheter shaft 104, an inflation lumen 105, and inflation ports 125 with the attached balloon 200. The balloon may be inflated from the single inflation lumen. The balloon 200 comprises balloon leg portions 204 as shown in FIG. 2. The balloon 200 is shown in FIG. 16C being inflated to a first intermediate diameter prior to the rupturing of the first frangible cover 1650a. The first frangible cover 1650a, second frangible cover 1650b, and third frangible cover 1650c are positioned sequentially around a balloon body portion 208 of the balloon 200. In other embodiments the first frangible cover 1650a, second frangible cover 1650b, and third frangible cover 1650c may extend over the balloon taper portions 206 and the balloon body portion 208 of the balloon 200.

The first intermediate diameter is smaller than the second intermediate diameter that is smaller than a third intermediate diameter which is smaller than a working diameter of the balloon 200. A working diameter of the balloon is defined as the maximum diameter of the inflated balloon.

The frangible balloon cover 1645 is positioned around balloon taper portions 206 and a balloon body portion 208 of the balloon 200.

The first frangible cover 1650a is operable to control the inflation of the balloon 200 to a first intermediate diameter that is larger than the pre-inflated diameter of the balloon 200. When the internal pressure of the balloon 200 reaches a first predetermined pressure the first frangible cover 1650a is operable to rupture permitting the balloon 200 to inflate to a second intermediate diameter larger than the first intermediate diameter (See FIGS. 17B and 17C).

Rupturing as defined herein is to brake, tear, distort or yield, and, as used with regard to the frangible cover, rupturing of the frangible cover is operable to release the balloon from a constrained diameter allowing the underlying balloon to expand to a larger diameter.

The second frangible cover 1650b is operable to control the inflation of the balloon 200 to a second intermediate diameter that is larger than the first intermediate diameter. When the internal pressure of the balloon 200 reaches a second predetermined pressure the second frangible cover 1650b is operable to rupture permitting the balloon 200 to inflate to a third intermediate diameter larger than the second intermediate diameter.

The third frangible cover 1650c is operable to control the inflation of the balloon 200 to a third intermediate diameter that is larger than the second intermediate diameter. When the internal pressure of the balloon 200 reaches a third predetermined pressure the third frangible cover 1650c is operable to rupture permitting the balloon 200 to inflate to the working diameter of the balloon 200 which is larger than the third intermediate diameter.

The first frangible cover 1650a, second frangible cover 1650b, and third frangible cover 1650c are shown in FIG. 16C having increasing thickness, respectively, as an example of imparting material strength to the frangible covers such that they rupture at increasingly higher pressures, respectively. It is understood and appreciated that rupture of the frangible cover at predetermined pressures may be affected by many means, including, but not limited to, material physical properties.

In accordance with an embodiment, the balloon cover assembly 1600c further comprises an optional outer cover 1616 that covers the first frangible cover 1650a, second frangible cover 1650b, and third frangible cover 1650c and balloon leg portions 204. The outer cover 1616 has a form substantially similar to the balloon as shown in FIG. 2. The outer cover 1616 may be coupled to the balloon leg portions 204. The outer cover 1616 is operable to contain any fragments or loose edges of the first frangible cover 1650a, second frangible cover 1650b, and third frangible cover 1650c that may form as a result of the frangible covers rupturing. The optional outer cover 1616 may also be operable to prevent a stent placed thereon from sliding along the length of the balloon cover.

In accordance with embodiments, the frangible cover is made of a material that has a very predictable elongation to break. In accordance with an embodiment, this elongation to break is very abrupt leading to complete failure with tear propagation allowing the frangible cover to fail in entirety. In accordance with an embodiment, a material has an elongation to break of <30%, or <20%, or preferably <15%. In accordance with an embodiment, the frangible cover is operable to have an elongation to fail that is approximately less than 15% of its manufactured diameter. That is to say, a frangible cover fabricated to a 14 mm diameter will provide an intermediate diameter that predictably will rupture at approximately 16 mm.

Figure 18A:
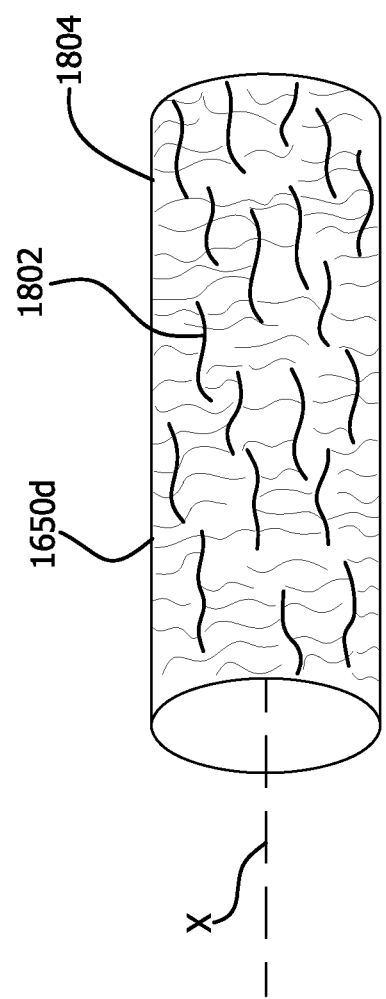
FIG. 18A is a side view of the frangible cover comprising elongated nodes, in accordance with an embodiment.

In accordance with an embodiment, a frangible cover comprises elements to allow the propagation of a tear completely across the frangible cover. FIG. 18A is a frangible cover 1650d comprising elongated nodes 1802 of ePTFE that are substantially oriented along a longitudinal axis of the frangible cover 1650d, or perpendicular to the applied hoop stress, in accordance with an embodiment. Such orientation allows for longitudinal tearing of the frangible cover 1650d at locations between the elongated nodes 1802.

In an alternate embodiment, the frangible cover comprises a material with a yield point followed by a high degree of lower load plastic deformation. For example, a frangible cover is operable to provide an intermediate inflation diameter of, by way of example, 14 mm-16 mm and operable to immediately yield upon distention, followed by at least 80% elongation at a lower load plateau to a final balloon diameter of 25 mm.

Figure 18B:
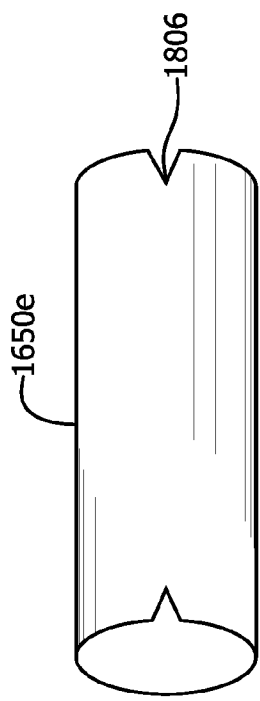
FIG. 18B is a side view of the frangible cover comprising notches, in accordance with an embodiment.
Figure 18D:
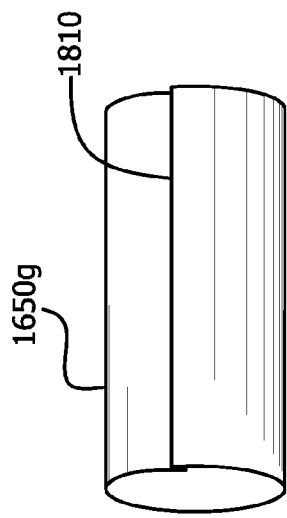
FIG. 18D is a side view of the frangible cover comprising a seam, in accordance with an embodiment.
Figure 18C:
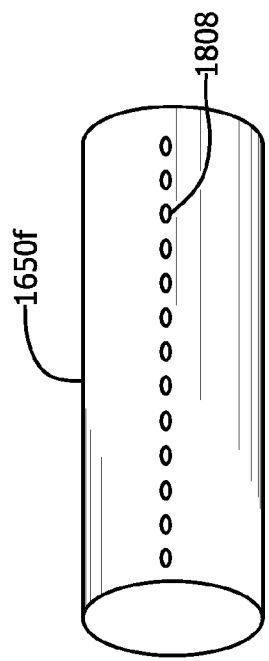
FIG. 18C is a side view of the frangible cover comprising perforations, in accordance with an embodiment.

In an alternate embodiment, the frangible cover comprises an element that is operable to cause abrupt failure of the frangible cover at a predictable load. In accordance with embodiments, this element includes, but not limited to, notches 1806 as provided in frangible cover 1650e as shown in FIG. 18B, perforations 1808 as provided in frangible cover 1650f as shown in FIG. 18C, holes, and densifications. In accordance with embodiments, this feature includes a seam, a joint 1810 as shown in FIG. 18D, or other means of holding the frangible cover in a tubular form until a predictable amount of load is applied.

In accordance with embodiments, additional frangible covers can be provided operable to cause multiple "spikes" similar to 1710 along the plateau 1712. The multiple frangible release layers can be tailored to split at specific diameters, such as at 20 mm, 25 mm etc.

Figure 19B:
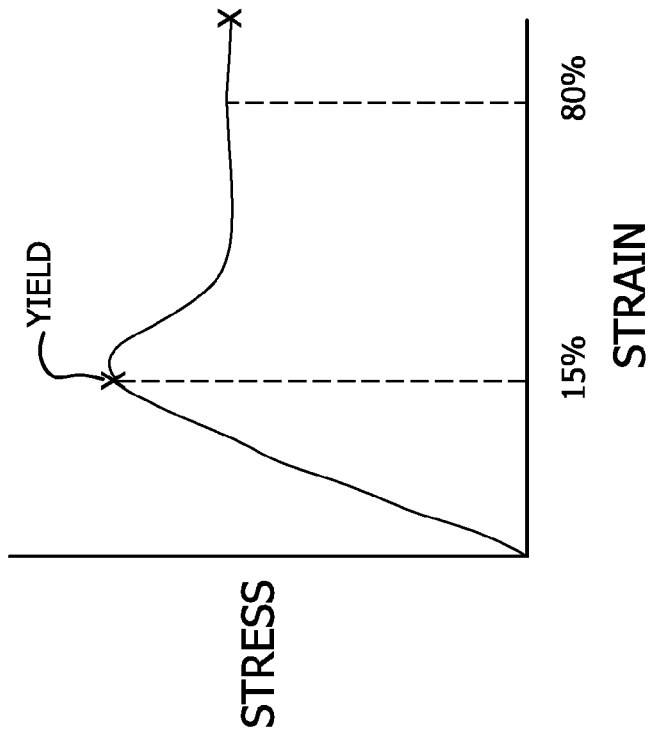
FIG. 19A is a frangible cover stress strain curve, in accordance with an embodiment.
Figure 19A:
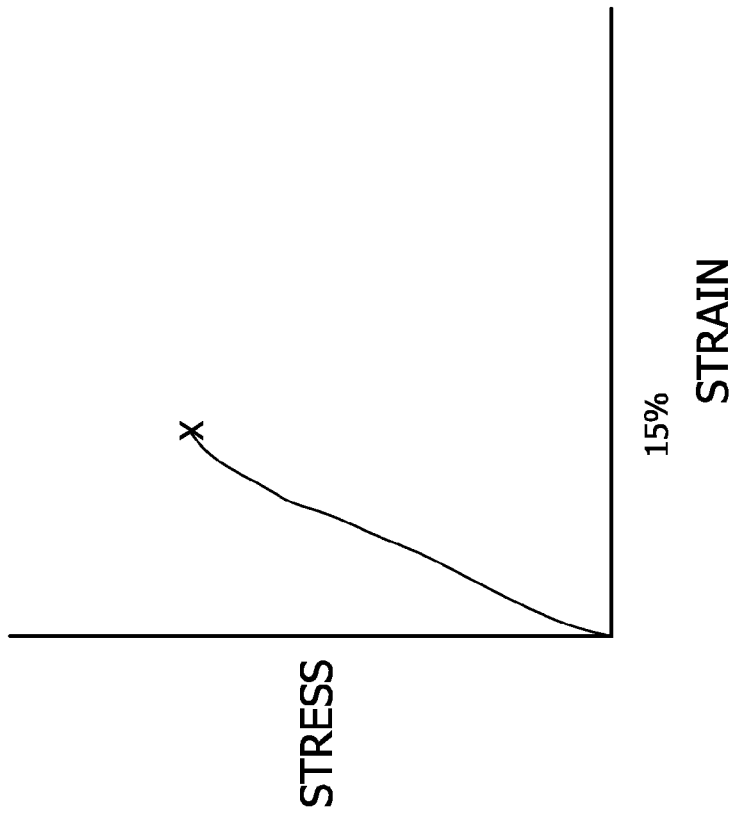

FIG. 19A is a stress-strain curve depicting a profile of a material property that would enable a frangible cover to control a balloon to an intermediate diameter then rupture. FIG. 19B is a stress-strain curve depicting a profile of a material property that would enable a frangible cover to control a balloon to an intermediate diameter then yield.

Example 5

The following describes an embodiment of a method utilizing thin, polymeric film lay-ups used to fabricate balloon covers in accordance with embodiments provided herein. This configuration is constructed in general accordance with the previously described methods and Example 1. This embodiment of the method includes the addition of balloon cover leg portions, the addition of a frangible cover along with the addition of an outer cover. This method can comprise the following steps:

Cover leg portions 1504, shown in FIG. 8B, were added to the first cover portion 313 and to the second cover portion 315.

Figure 14A:
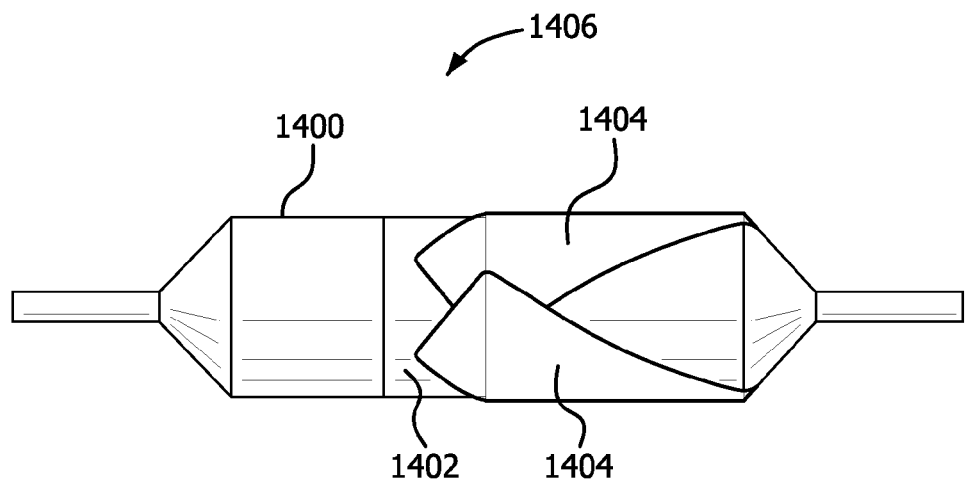
FIGS. 14A and 14B are side views of an assembly comprising a mandrel and a film lay-up strap, in accordance with an embodiment.

An assembly as shown in FIG. 14 was provided. The assembly 1406 comprises a mandrel 1400, a wrapped manufacturing aid 1402 and three polymeric film straps 1404. The assembly 1406 was formed using the materials and process as previously described in Example 1.

Figure 14B:
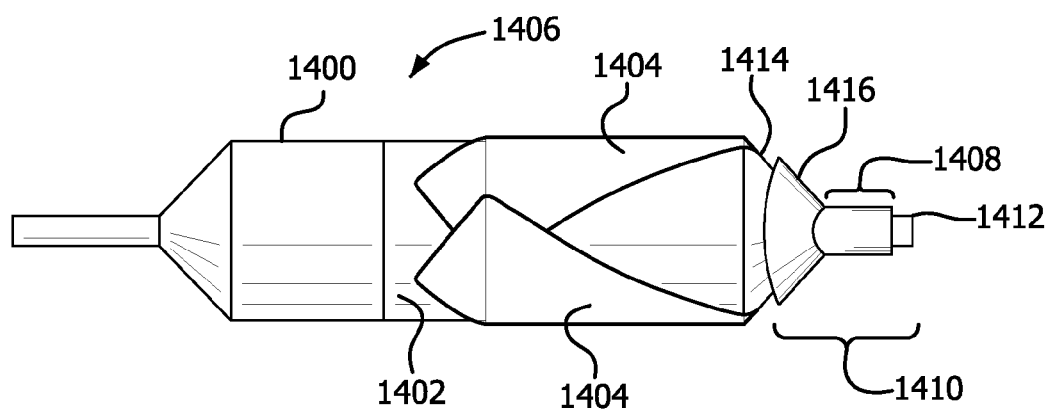

As shown in FIG. 14B, a cover leg portion 1408 was added to the assembly 1406. A thin-walled, radially expandable ePTFE tube 1410 was stretched over the mandrel shaft 1412 and partially up onto the mandrel taper portion 1414. The tube 1410 partially covered the three polymeric film straps 1404. The thin-walled ePTFE tube 1410 had an initial diameter of about 4 mm and a length of about 50 mm. The excess length of the tubing 1410 was trimmed to expose about 10 mm of the mandrel shaft 1412.

A circumferential film wrap was then added according to previously described Example 1. Three additional film straps were then added according to previously described Example 1. The three additional film straps covered the taper portion 1416 of the thin-walled, radially expandable ePTFE tube 1410.

Similarly, a cover leg portion 1408 was then added to the opposing mandrel end following previously described assembly in Example 1, resulting in a pair of balloon covers as shown in FIG. 8B. As shown in FIG. 8B, a first cover body portion 312 have a first cover body portion 312 having a working length 802 integrally connected to a first cover taper portion 314. The first cover taper portion 314 has a cover leg portion 1504 located at an apex of the first cover taper portion 314. Also shown in FIG. 8B is a second cover portion 315 having a second cover body portion 318 having a working length 1512 integrally connected to a second cover taper portion 320. The second cover taper portion 320 has a cover leg portion 1504 located at an apex of the second cover taper portion 320.

As further shown in FIG. 8B, the second cover portion 315 can be inserted into the first cover portion 313 by translating the second body portion 318 into the first cover body portion 312 as indicated by direction arrows (820, 822), so that the first cover body portion 312 and the second body portion 318 are substantially overlapped (as previously defined).

The first cover body portion 312 and the second body portion 318 were then bonded together along the working lengths according to Example 1.

A compacted and folded PET balloon was then inserted into the bonded first cover body portion 312 and second cover portion 315 according to previous Example 1. In this embodiment the cover leg portions 1504 were bonded to the underlying balloon leg portions 204. No adhesive was injected between the first and second cover body portions and the balloon body portion. To bond the first and second cover leg portions to the balloon leg portions, an ePTFE film was imbibed with an adhesive and the film was then wrapped around the balloon leg portions. The ePTFE film had a high degree of longitudinal strength, was about 6 mm wide and was imbibed with LOCTITE® 4981 adhesive. Hand tension was applied to the film as the film was wrapped around the balloon leg portions. Five layers of film were applied.

A frangible cover was then applied to the balloon cover. An ePTFE film tube was formed by longitudinally wrapping nine layers of a 90 mm wide film onto a 14 mm mandrel. The film had an elongation to break of approximately 12% (7%-17%), and a maximum tensile load of roughly 1.2 (0.7 to 1.7) pounds per linear inch. The longitudinally wrapping is also referred to as a "cigarette" wrap. The precursor material and film are described in U.S. Pat. No. 5,708,044 to Branca and in U.S. Pat. No. 5,814,405 to Branca et al., both of which are incorporated by reference herein in their entirety. The film was oriented such that its fibrils were aligned with the circumference, which provides a high degree of resistance to elongation during inflation allowing the balloon to build pressure until that of about 5 atm. The film was oriented such that its long nodes were oriented perpendicular to the circumference providing a means for complete tear propagation along the length of the frangible cover when the frangible cover is taken past its maximum inflation pressure or to a diameter past that of approximately 16 mm. The frangible cover was then positioned over the balloon cover. The frangible cover had a length that approximated the overall balloon length, minus the lengths of the balloon leg portions as shown in FIG. 16A. The radial force required to split the frangible cover can be set by varying the number of layers of a given frangible film that comprises the frangible cover.

An outer cover was then added to cover the frangible cover. The outer cover was fabricated by the following process:

An ePTFE film was helically wrapped around a mandrel having a diameter of about 25 mm and a length of about 37 cm. The film width was about 2.54 cm. Twenty layers were wrapped in a helical pattern having a 1.85° pitch angle. The wrapped length was about 30 cm.

The film wrapped mandrel was then placed into an air convection oven heated to about 380° C. for about 25 minutes. This heat exposure bonded the layers of ePTFE, forming a thin film tube.

The ePTFE film wrapped mandrel was removed from the oven, allowed to cool, and the thin film tube was removed from the mandrel. The thin film tube had a diameter of about 25 mm and a wall thickness of about 0.0254 mm.

The about 30 cm long thin film tube was then tensioned by hand and stretched longitudinally to about 400% of the original length, or to about 120 cm. After stretching, the tube was placed onto a mandrel having a diameter of about 4 mm and a length of about 130 cm. The stretched tube was smoothed by hand onto the mandrel, forming a small diameter thin film tube having a diameter of about 4 mm.

A temporary ePTFE film was then helically wrapped onto the about 4 mm diameter thin wall tube. The film thickness was about 0.00508 mm and the film width was about 1.905 cm. One pass of film was wrapped, using a 2.6924 mm pitch (measured from adjacent film edges) with a film angle of about 78°.

The thin film tube and temporary ePTFE film wrap was then longitudinally compressed by 40%, from a starting length of about 130 cm to a compressed length of about 78 cm.

The longitudinally compressed thin film tube and mandrel was then placed into an air convection oven heated to about 380° C. for about 1 minute.

The ePTFE film wrapped mandrel was then removed from the oven and allowed to cool.

The temporary ePTFE film wrap was then removed from the thin film tube.

The outer cover was then positioned onto the frangible cover. The outer cover had a length that approximated the overall balloon length as shown in FIG. 16A. The ends of the outer cover were aligned to the ends of the balloon leg portions.

The outer cover was then bonded to the underlying frangible cover using an ePTFE film imbibed with an adhesive. The imbibed film was wrapped around the underlying balloon cover leg portions. The ePTFE film had a high degree of longitudinal strength, was about 6 mm wide and was imbibed with LOCTITE® 4981 adhesive. Hand tension was applied to the film as five layers of film were applied.

The resulting covered balloon had a cross-section as shown in FIG. 16A and as previously described. A PET balloon 200 is bonded to the catheter shaft 104 with an adhesive 1608 along the balloon leg portions 204. A first cover portion 313 and a second cover portion 315 are shown covering the PET balloon 200. The first cover portion 313 and a second cover portion 315 are joined along a bond line 1610. The cover leg portions of the first cover portion 313 and a second cover portion 315 are bonded to the PET balloon 200 by an adhesive imbibed film 1612. The frangible cover 1650 is shown surrounding the first cover portion 313 and a second cover portion 315. An outer cover 1616 is shown covering the frangible cover 1650. The outer cover 1616 is shown bonded to the cover leg portions by an adhesive imbibed film 1618.

Testing of the device of Example 5 provided a balloon diameter vs. pressure profile substantially as shown in FIG. 15A, generally depicting an inflation sequence 1700 of the balloon described in FIG. 16. The balloon had an initial diameter of about 4 mm indicated as 1702. As pressure was applied to the balloon, the balloon began to expand. The balloon diameter increased as the frangible cover began to resist further expansion when the balloon diameter reached about 14 mm (1708). The frangible cover split (1710) at about 5 atm while at an approximate 14 mm diameter. The balloon then continued to expand in diameter (1712) while at an approximate pressure of 2 Atm. At a diameter of about 25 mm, the first cover portion 313 and a second cover portion 315 began to resist further expansion (1714). As the pressure was increased to above 2 atm, the balloon remained at essentially 25 mm (1716). At a pressure of about 10 atm, the balloon burst (1718).

Numerous characteristics and advantages of the present invention have been set forth in the preceding description, including preferred and alternate embodiments together with details of the structure and function of the invention. The disclosure is intended as illustrative only and as such is not intended to be exhaustive. It will be evident to those skilled in the art that various modifications may be made, especially in matters of structure, materials, elements, components, shape, size and arrangement of parts within the principals of the invention, to the full extent indicated by the broad, general meaning of the terms in which the appended claims are expressed. To the extent that these various modifications do not depart from the spirit and scope of the appended claims, they are intended to be encompassed therein. In addition to being directed to the embodiments described above and claimed below, the present invention is further directed to embodiments having different combinations of the features described above and claimed below. As such, the invention is also directed to other embodiments having any other possible combination of the dependent features claimed below.

What is claimed is:
1. A catheter balloon assembly comprising:
an inflatable balloon comprising a balloon body portion defining a balloon working length and an un-inflated diameter and a working diameter; and
a frangible cover covering at least a portion of an outer surface of the balloon body portion and extending beyond the balloon working length, the frangible cover being operable to rupture under an internal pressure before a rupture of the balloon wherein, prior to rupture, the frangible cover is operable to control the balloon to open to an intermediate diameter that is substantially uniform along the working length that is less than the working diameter, the frangible cover having a diameter that is the same as the intermediate diameter; and
an outer cover covering at least a substantial portion of the frangible cover operable to contain the frangible cover once the frangible cover ruptures during use within a passageway of a patient's body, wherein an inner surface of the frangible cover is in contact with the outer surface of the balloon body along at least a portion of the balloon working length.

2. The catheter balloon assembly of claim 1 further comprising a plurality of frangible covers each being operable to control the balloon to open sequentially to a different larger intermediate diameter that is smaller than the working diameter.

3. The catheter balloon assembly of claim 1 wherein the balloon increases in diameter substantially uniformly along the working length of the balloon after the rupture of the frangible cover.

4. The catheter balloon assembly of claim 1, wherein the balloon is a compliant balloon.

5. The catheter balloon assembly of claim 1, wherein the balloon is a non-compliant balloon.

6. The catheter balloon assembly of claim 1, the balloon comprising two opposed balloon leg portions that are each integrally connected to a balloon taper portion, with each of the balloon taper portions connected to a balloon body portion therebetween, the balloon working length defined as the length of the balloon body portion of the balloon that comprises an approximate length between opposed balloon taper portions;

further comprising a balloon cover comprising:

a first legged cover portion including a first cover body portion integrally connected to a first cover taper portion, further including a cover leg portion located at an apex of the first cover taper portion, the first cover body portion being operable to overlay a portion of the balloon body portion, the first cover taper portion being operable to overlay a portion of the balloon taper portion, the cover leg portion being operable to allow the leg portion of the balloon to pass through; and a second legged cover portion including a second cover body portion integrally connected to a second cover taper portion, further including a cover leg portion located at an apex of the second cover taper portion the second cover body portion being operable to overlay a portion of the balloon body portion, the second cover taper portion being operable to overlay a portion of the balloon taper portion, the cover leg portion being operable to allow the leg portion of the balloon to pass through, the first cover taper portion and the second cover taper portion are located at opposite ends of the balloon cover, the first cover portion and the second cover portion are coaxially aligned along axis X and overlay the balloon such that at least a portion of the first cover body portion overlays at least a portion of the second cover body portion, the frangible cover overlaying the first cover body portion, the second cover body portion, and at least a portion of each of the first cover taper portion and the second cover taper portion, the outer cover covers the frangible cover and is coupled to the first cover leg portion and the second cover leg portion.

7. The catheter balloon assembly of claim 6, wherein the balloon cover comprises a fibrillated material.

8. The catheter balloon assembly of claim 7, wherein the fibrillated material is ePTFE.

9. The catheter balloon assembly of claim 8, wherein fibrils in said ePTFE are oriented in a radial direction.

10. The catheter balloon assembly of claim 8, wherein the balloon cover is made from strips of ePTFE that are adhered to each other.

11. The catheter balloon of claim 10, wherein the strips are laid in multiple angular orientations on the working length and the cover taper portions.

12. The catheter balloon of claim 6, wherein the balloon cover is adhered to the balloon.

13. The catheter balloon of claim 6, wherein the cover body portions that overlap for at least a substantial portion of the balloon body portion also cover a portion of balloon taper portion.

14. The catheter balloon of claim 6, wherein the working diameter of the balloon cover is smaller than the working diameter of the balloon.

15. The catheter balloon of claim 1, wherein the inflation of the balloon is provided by a single inflation lumen.

16. The catheter balloon of claim 1, wherein the intermediate diameter is greater than 20% of the working diameter.

17. The catheter balloon of claim 1, wherein the intermediate diameter is greater than 30% of the working diameter.

18. The catheter balloon of claim 1, wherein the intermediate diameter is greater than 50% of the working diameter.

19. A frangible balloon assembly comprising:

a catheter shaft including an inflation lumen in fluid communication with an inflation port;

a balloon coupled to the catheter shaft and in fluid communication with the inflation port, the balloon including a balloon body portion and a balloon working length, the balloon having a working diameter; and a frangible cover covering at least a portion of an outer surface of the balloon body portion and extending beyond the balloon working length, the frangible cover being operable to restrain the balloon to an intermediate diameter that is smaller than the working diameter up to a predetermined pressure, the frangible cover operable to rupture at the predetermined pressure to allow the balloon to expand to the working diameter; and an outer cover covering at least a substantial portion of the frangible cover operable to contain the frangible cover once the frangible cover ruptures during use within a passageway of a patient's body, wherein, prior to rupture, the frangible cover is operable to control the balloon to open to an intermediate diameter that is substantially uniform along the working length that is less than the working diameter, the frangible cover having a diameter that is the same as the intermediate diameter, wherein the frangible cover has a smooth outer surface at the intermediate diameter.

20. The frangible balloon assembly of claim 19, further comprising a plurality of frangible covers each being operable to control the balloon to open sequentially to a different larger intermediate diameter that is smaller than the working diameter.

21. The frangible balloon assembly of claim 19, wherein the balloon increases in diameter substantially uniformly along the working length of the balloon after the rupture of the frangible cover.

22. The frangible balloon assembly of claim 19, wherein the balloon is a compliant balloon.

23. The frangible balloon assembly of claim 19, wherein the balloon is a non-compliant balloon.

24. The frangible balloon assembly of claim 19, the balloon comprising two opposed balloon leg portions that are each integrally connected to a balloon taper portion, with each of the balloon taper portions connected to a balloon body portion therebetween, the balloon working length defined as the length of the balloon body portion of the balloon that comprises an approximate length between opposed balloon taper portions;

further comprising a balloon cover comprising:
- a first legged cover portion including a first cover body portion integrally connected to a first cover taper portion, further including a cover leg portion located at an apex of the first cover taper portion, the first cover body portion being operable to overlay a portion of the balloon body portion, the first cover taper portion being operable to overlay a portion of the balloon taper portion, the cover leg portion being operable to allow the leg portion of the balloon to pass through; and
- a second legged cover portion including a second cover body portion integrally connected to a second cover taper portion, further including a cover leg portion located at an apex of the second cover taper portion the second cover body portion being operable to overlay a portion of the balloon body portion, the second cover taper portion being operable to overlay a portion of the balloon taper portion, the cover leg portion being operable to allow the leg portion of the balloon to pass through, the first cover taper portion and the second cover taper portion are located at opposite ends of the balloon cover, the first cover portion and the second cover portion are coaxially aligned and overlay the balloon such that at least a portion of the first cover body portion overlays at least a portion of the second cover body portion, the frangible cover overlaying the first cover body portion, the second cover body portion, and at least a portion of each of the first cover taper portion and the second cover taper portion, the outer cover covers the frangible cover and is coupled to the first cover leg portion and the second cover leg portion.

25. The frangible balloon assembly of claim 24, wherein the balloon cover comprises a fibrillated material.

26. The frangible balloon assembly of claim 25, wherein the fibrillated material is ePTFE.

27. The frangible balloon assembly of claim 26, wherein fibrils in said ePTFE are oriented in a radial direction.

28. The frangible balloon assembly of claim 26, wherein the balloon cover is made from strips of ePTFE that are adhered to each other.

29. The frangible balloon of claim 28, wherein the strips are laid in multiple angular orientations on the working length and the cover taper portions.

30. The frangible balloon of claim 28, wherein the balloon cover is adhered to the balloon.

31. The frangible balloon of claim 28, wherein the cover body portions that overlap for a substantial portion of the balloon body portion also cover a portion of balloon taper portion.

32. The frangible balloon of claim 28, wherein the working diameter of the balloon cover is smaller than the working diameter of the balloon.

33. A catheter balloon assembly comprising:
- an inflatable balloon having a balloon body portion defining a balloon working length, the inflatable also having an un-inflated diameter and a working diameter; and
- a frangible cover covering at least a portion of an outer surface of the balloon body portion and extending beyond the balloon working length, the frangible cover being operable to rupture under an internal pressure before a rupture of the balloon, wherein, prior to rupture, the frangible cover is operable to control the balloon to open to an intermediate diameter that is substantially uniform along the working length that is less than the working diameter, the frangible cover having a diameter that is the same as the intermediate diameter;
- an outer cover covering at least a substantial portion of the frangible cover operable to contain the frangible cover once the frangible cover ruptures during use within a passageway of a patient's body,
- wherein the catheter balloon assembly is operable to provide a balloon diameter vs. balloon pressure profile having a balloon inflation sequence providing a first intermediate inflated diameter and the working diameter of the inflatable balloon such that the inflatable balloon attains the first intermediate diameter at a first predetermined pressure, and attains the working diameter at a final predetermined pressure that is lower than the first predetermined pressure, and
- wherein the frangible cover is flush with the at least a portion of the outer surface of the balloon body portion.

34. The catheter balloon assembly of claim 33 further comprising a plurality of frangible covers each being operable to control the balloon to open sequentially to a different larger intermediate diameter that is smaller than the working diameter.

35. The catheter balloon assembly of claim 33 wherein the balloon increases in diameter substantially uniformly along the working length of the balloon after the rupture of the frangible cover.

36. The catheter balloon assembly of claim 33, wherein the balloon is a compliant balloon.

37. The catheter balloon assembly of claim 33, wherein the balloon is a non-compliant balloon.

38. The catheter balloon assembly of claim 33, the balloon comprising two opposed balloon leg portions that are each integrally connected to a balloon taper portion, with each of the balloon taper portions connected to a balloon body portion therebetween, the balloon working length defined as the length of the balloon body portion of the balloon that comprises an approximate length between opposed balloon taper portions;

further comprising a balloon cover comprising: a first legged cover portion including a first cover body portion integrally connected to a first cover taper portion, further including a cover leg portion located at an apex of the first cover taper portion, the first cover body portion being operable to overlay a portion of the balloon body portion, the first cover taper portion being operable to overlay a portion of the balloon taper portion, the cover leg portion being operable to allow the leg portion of the balloon to pass through; and
a second legged cover portion including a second cover body portion integrally connected to a second cover taper portion, further including a cover leg portion located at an apex of the second cover taper portion the second cover body portion being operable to overlay a portion of the balloon body portion, the second cover taper portion being operable to overlay a portion of the balloon taper portion, the cover leg portion being operable to allow the leg portion of the balloon to pass through, the first cover taper portion and the second cover taper portion are located at opposite ends of the balloon cover, the first cover portion and the second cover portion are coaxially aligned and overlay the balloon such that at least a portion of the first cover body portion overlays at least a portion of the second cover body portion, the frangible cover overlaying the first cover body portion, the second cover body portion, and at least a portion of each of the first cover taper portion and the second cover taper portion, the outer cover covers the frangible cover and is coupled to the first cover leg portion and the second cover leg portion.

39. The catheter balloon assembly of claim 38, wherein the balloon cover comprises a fibrillated material.

40. The catheter balloon assembly of claim 39, wherein the fibrillated material is ePTFE.

41. The catheter balloon assembly of claim 40, wherein fibrils in said ePTFE are oriented in a radial direction.

42. The catheter balloon assembly of claim 40, wherein the balloon cover is made from strips of ePTFE that are adhered to each other.

43. The catheter balloon assembly of claim 42, wherein the strips are laid in multiple angular orientations on the working length and the first cover taper portion and second cover taper portion.

44. The catheter balloon assembly of claim 38, wherein the balloon cover is adhered to the balloon.

45. The catheter balloon assembly of claim 38, wherein the cover body portions that overlap for a substantial portion of the balloon body portion also cover a portion of balloon taper portion.

46. The catheter balloon assembly of claim 38, wherein the working diameter of the balloon cover is smaller than the working diameter of the balloon.

47. The catheter balloon assembly of claim 1, wherein the inflatable balloon further comprises two opposed balloon leg portions that are each integrally connected to a balloon taper portion, with each of the balloon taper portions being connected to the balloon body portion therebetween, and the frangible cover only covers the outer surface of the balloon body portion and at least a portion of an outer surface of each of the balloon taper portions.

48. The catheter balloon assembly of claim 47, wherein the outer cover covers the frangible cover and the two opposed balloon leg portions such that the outer cover is configured to contain the frangible cover once the frangible cover ruptures, wherein the two opposed balloon leg portions are bonded to a catheter shaft and the outer cover is coupled to the two opposed balloon leg portions.

49. The catheter balloon assembly of claim 47, wherein the two opposed balloon leg portions are bonded to a catheter shaft and the frangible cover comprises expanded polytetrafluoroethylene (ePTFE).

50. The catheter balloon assembly of claim 1, wherein after rupture the frangible cover is not operable to control the balloon to open to a second intermediate diameter that is greater than the intermediate diameter.

51. The catheter balloon assembly of claim 1, further comprising an endoprosthesis on an outer surface of the frangible cover.

52. The catheter balloon assembly of claim 1, wherein the frangible cover comprises a fibrillated material.

* * * * *